US009980690B2

(12) United States Patent
Muroi et al.

(10) Patent No.: US 9,980,690 B2
(45) Date of Patent: May 29, 2018

(54) MEDICAL DIAGNOSTIC IMAGING APPARATUS

(71) Applicant: Toshiba Medical Systems Corporation, Otawara-shi (JP)

(72) Inventors: Toshio Muroi, Nasushiobara (JP); Manabu Tanaka, Otawara (JP); Yoshinori Shimizu, Nasushiobara (JP); Takuya Sakaguchi, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 586 days.

(21) Appl. No.: 14/448,044

(22) Filed: Jul. 31, 2014

(65) Prior Publication Data
US 2014/0341350 A1 Nov. 20, 2014

Related U.S. Application Data

(63) Continuation of application No. PCT/JP2013/052412, filed on Feb. 1, 2013.

(30) Foreign Application Priority Data

Feb. 1, 2012 (JP) ................................ 2012-020026
Feb. 1, 2013 (JP) ................................ 2013-018709

(51) Int. Cl.
*G01N 23/04* (2018.01)
*A61B 6/00* (2006.01)
*A61B 6/06* (2006.01)

(52) U.S. Cl.
CPC ............... *A61B 6/463* (2013.01); *A61B 6/06* (2013.01); *A61B 6/504* (2013.01); *A61B 6/52* (2013.01); *A61B 6/545* (2013.01); *A61B 6/5235* (2013.01)

(58) Field of Classification Search
CPC .......... A61B 6/06; A61B 6/463; A61B 6/504; A61B 6/52; A61B 6/5235; A61B 6/545;
(Continued)

(56) References Cited

U.S. PATENT DOCUMENTS 5,012,504 A * 4/1991 McFaul ................ H04N 5/2351
348/E5.035
5,619,042 A 4/1997 Hughes
(Continued)

FOREIGN PATENT DOCUMENTS

JP 09-028822 A 2/1997
JP 09028822 A * 2/1997 ............... A61N 5/10
(Continued)

OTHER PUBLICATIONS

International Search Report dated Apr. 9, 2013 for PCT/JP2013/052412 Filed on Feb. 1, 2013 (English Translation).
(Continued)

*Primary Examiner* — Irakli Kiknadze
(74) *Attorney, Agent, or Firm* — Oblon, McClelland, Maier & Neustadt, L.L.P.

(57) ABSTRACT

According to embodiments, in a medical diagnostic imaging apparatus, an imaging unit captures a subject in a second X-ray irradiation area narrower than a first X-ray irradiation area. An X-ray image generating unit generates a first X-ray image in the first X-ray irradiation area and a second X-ray image in the second X-ray irradiation area based on an imaging result by the imaging unit. The adjusting unit calculates a statistic of a pixel value of the first X-ray image and adjusts an operating condition of the imaging unit so that the statistic approaches a threshold. A control unit causes the imaging unit and the X-ray image generating unit to generate the X-ray image based on the adjusted operating condition. Subsequently, the control unit performs control for
(Continued)

causing the imaging unit and the X-ray image generating unit to generate the second X-ray image based on the operating condition.

20 Claims, 16 Drawing Sheets

(58) Field of Classification Search
CPC ..... A61B 6/481; A61B 6/5205; A61B 6/4441; A61B 6/032; A61B 6/5217; A61B 6/487; A61B 6/486; A61B 6/461; A61B 6/542; A61B 6/469; A61B 6/5211; A61B 6/467; A61B 5/23293; A61B 5/2354; G09G 2360/145; G09G 3/3406; H04N 5/23293; H04N 5/2354
USPC ............................ 378/62, 98.7, 147, 156, 207
See application file for complete search history.

(56) References Cited

U.S. PATENT DOCUMENTS

| | | | | |
|---|---|---|---|---|
| 7,197,107 B2* | 3/2007 | Arai | ................ | A61B 6/032 378/15 |
| 7,639,776 B2* | 12/2009 | Gohno | ................ | A61B 6/032 378/109 |
| 7,689,266 B2* | 3/2010 | Shinohara | ................ | A61B 6/00 378/4 |
| 2004/0141582 A1 | 7/2004 | Ono | | |
| 2008/0056547 A1* | 3/2008 | Kokubun | ................ | A61B 6/032 382/128 |
| 2009/0141854 A1* | 6/2009 | Hirokawa | ................ | A61B 6/032 378/4 |

FOREIGN PATENT DOCUMENTS

| | | | | |
|---|---|---|---|---|
| JP | 2003-115399 A | | 4/2003 | |
| JP | 2003115399 A | * | 4/2003 | ................ A61B 6/00 |
| JP | 2005-198798 A | | 7/2005 | |
| JP | 2005198798 A | * | 7/2005 | |
| JP | 2007-159913 A | | 6/2007 | |
| JP | 2007159913 A | * | 6/2007 | |
| JP | 2009-261684 A | | 11/2009 | |
| JP | 2009261684 A | * | 11/2009 | ................ A61B 6/00 |
| JP | 2009-279289 A | | 12/2009 | |
| JP | 2009279289 A | * | 12/2009 | ................ A61B 6/03 |
| JP | 2010-246794 A | | 11/2010 | |
| JP | 2010246794 A | * | 11/2010 | |
| JP | 2010-273834 A | | 12/2010 | |
| JP | 2010273834 A | * | 12/2010 | |

OTHER PUBLICATIONS

International Written Opinion dated Apr. 9, 2013 for PCT/JP2013/052412 Filed on Feb. 1, 2013.
International Search Report dated Apr. 9, 2013 for PCT/JP2013/052412 filed Feb. 1, 2013 (English Translation).
International Written Opinion dated Apr. 9, 2013 for PCT/JP2013/052412 filed Feb. 1, 2013.

* cited by examiner

FIG.5
(A)
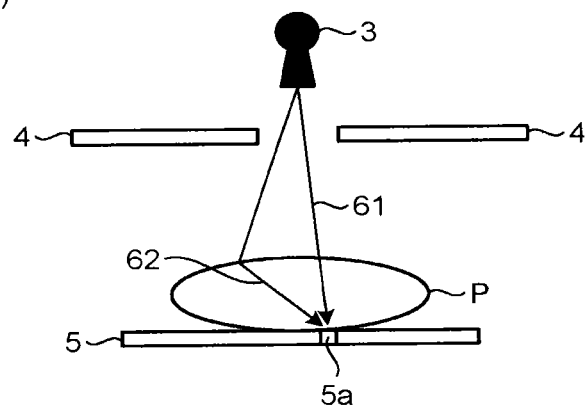
(B)
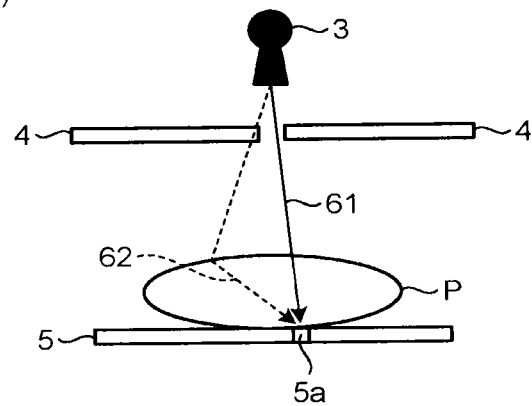

MEDICAL DIAGNOSTIC IMAGING APPARATUS

CROSS-REFERENCE TO RELATED APPLICATIONS

This application is a continuation of PCT international application Ser. No. PCT/JP2013/052412 filed on Feb. 1, 2013 which designates the United States, incorporated herein by reference, and which claims the benefit of priority from Japanese Patent Application No. 2012-020026, filed on Feb. 1, 2012, and Japanese Patent Application No. 2013-018709, filed on Feb. 1, 2013, the entire contents of which are incorporated herein by reference.

FIELD

Embodiments described herein relate generally to a medical diagnostic imaging apparatus.

BACKGROUND

A medical diagnostic imaging apparatus is an apparatus for imaging (fluoroscopic images, tomographic images, blood flow images, and the like) information in the body of a subject. Examples of the medical diagnostic imaging apparatus include an X-ray diagnosis apparatus, an X-ray CT apparatus, an MRI apparatus, and an ultrasonic diagnosis apparatus.

For example, an X-ray diagnosis apparatus delivers X-rays to a subject arranged between an X-ray source and an X-ray detecting unit that are oppositely arranged. The X-ray diagnosis apparatus detects X-rays passing through the subject and generates a medical image based on the detection result.

An angiosystem is known as an example of the X-ray diagnosis apparatus. For example, an angiosystem is used for seeing through the vascular morphology and the state of blood flow of a subject into which a contrast material is injected. An operator inserts a catheter and the like into a blood vessel of the subject while observing a fluoroscopic image thereof. A radiodiagnosis technique such as an X-ray angiosystem or a CT angiosystem (CT angiography, CTA) can be applied to a diagnosis, a treatment action, drainage, supply, and the like as interventional radiology (IVR).

Some X-ray diagnosis apparatuses such as an angiosystem can implement automatic brightness control. The automatic brightness control is processing for optimizing the brightness of a fluoroscopic image. Hereinafter, the automatic brightness control may be referred to as the automatic brightness control (ABC). An X-ray diagnosis apparatus stores therein a set value of a brightness level used for the ABC in advance. The brightness level of a fluoroscopic image is adjusted based on the set value and is reflected in the clarity or sharpness of the image.

More specifically, in the ABC, the X-ray diagnosis apparatus acquires a brightness level value (for example, the average value of the brightness level) of the fluoroscopic image based on transmitted X-rays obtained through X-rays irradiation. The X-ray diagnosis apparatus reads out the set value stored in advance, and compares it to the brightness level value of the fluoroscopic image. In a case where the brightness level value is different from the set value, the X-ray diagnosis apparatus changes fluoroscopy radiation conditions (imaging condition) in fluoroscopy so that the brightness level value is equal to the set value. The fluoroscopy radiation conditions include the irradiation time of X-rays (s) and the tube current (A), or the product of the irradiation time by the tube current (mAs), and the tube voltage (kV).

An X-ray imaging technique called partial fluoroscopy is also known. In partial fluoroscopy, fluoroscopy is performed in a relatively large area, and thereafter, a smaller region of interest (ROI) is set. Then a fluoroscopic image (sometimes referred to as a "partial fluoroscopic image") in the region of interest is synthesized with a last image hold (LIH) image and the like, and displayed.

An LIH image is a static image representing the state of the periphery (background) of the region of interest for partial fluoroscopy, and is the last image (frame) in the fluoroscopy before the partial fluoroscopy. The partial fluoroscopy employs such an LIH image and the like as the background and continues performing fluoroscopy only in an area particularly focused, so that X-rays are not delivered to a portion that does not need to be irradiated, thereby reducing the dose of radiation exposure of the subject.

BRIEF DESCRIPTION OF THE DRAWINGS

FIG. 5 is a diagram for explaining a problem according to the related art;

DETAILED DESCRIPTION

According to embodiment, a medical diagnostic imaging apparatus comprising, an imaging unit, an X-ray image generating unit, an adjusting unit and a control unit. The imaging unit configured to capture a subject in a second X-ray irradiation area that is narrower than a first X-ray irradiation area after imaging the subject in the first X-ray irradiation area. The X-ray image generating unit configured to generate a first X-ray image in the first X-ray irradiation area and a second X-ray image in the second X-ray irradiation area based on an imaging result by the imaging unit. The adjusting unit configured to calculate a statistic of a pixel value of the first X-ray image or the second X-ray image and adjust an operating condition of the imaging unit so that the statistic approaches a threshold set in advance. The control unit configured to control the imaging unit and the X-ray image generating unit so as to generate the second X-ray image based on the adjusted operating condition after generating the first X-ray image.

Hereinafter, medical diagnostic imaging apparatuses according to a first embodiment to a sixth embodiment will be described with reference to FIG. 1 to FIG. 16.

First Embodiment

With reference to FIG. 1 to FIG. 8, the configuration of a medical diagnostic imaging apparatus according to the first embodiment will be described by taking an X-ray diagnosis apparatus as a main example.

Overview of Entire X-Ray Diagnosis Apparatus

Figure 1:
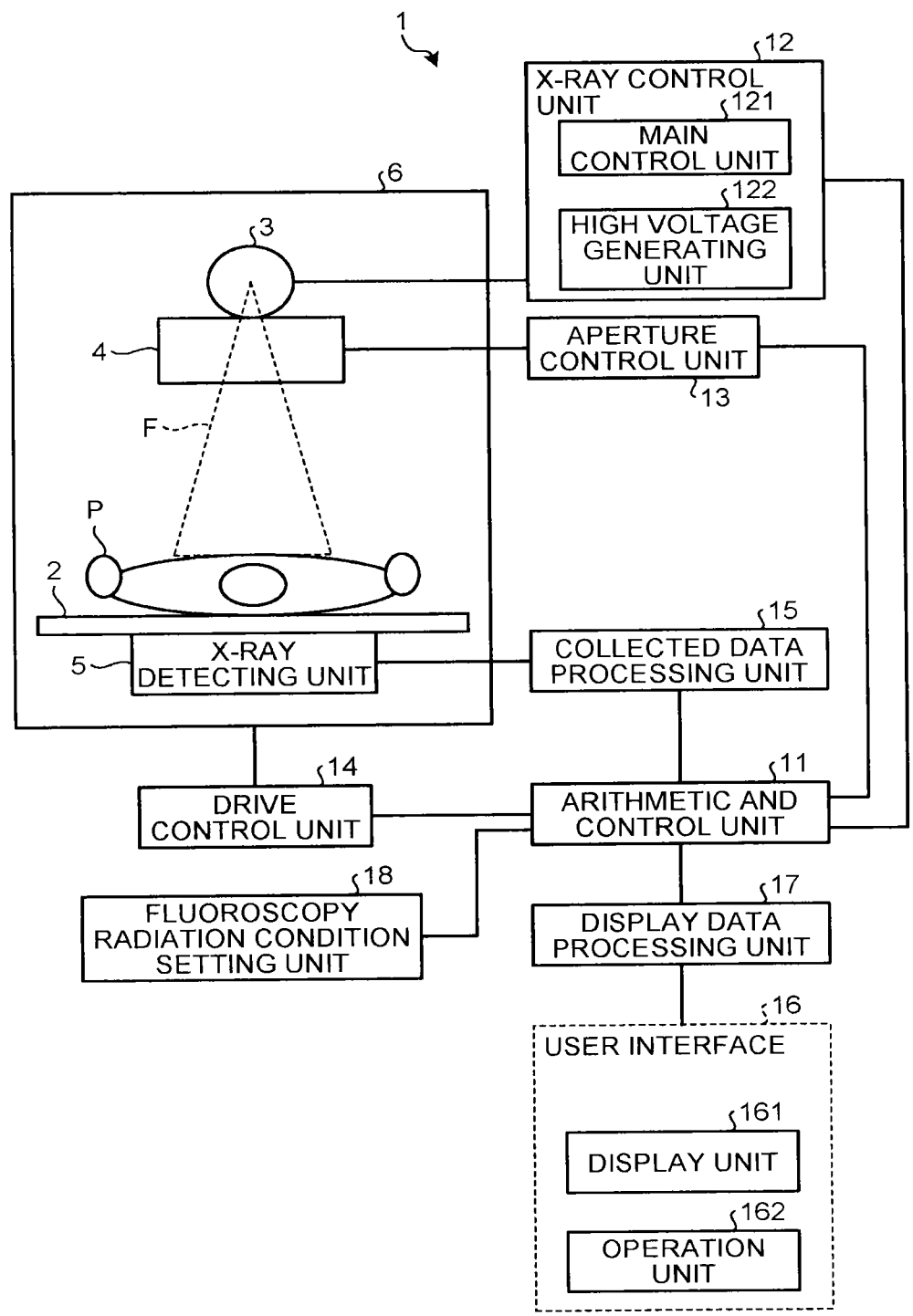
FIG. 1 is a schematic block diagram illustrating the entire configuration of an X-ray diagnosis apparatus according to an embodiment.

FIG. 1 is a schematic block diagram illustrating the entire configuration of the X-ray diagnosis apparatus according to the embodiment. This X-ray diagnosis apparatus 1 illustrated in the figure includes a couch 2, an X-ray tube 3, an X-ray aperture 4, and an X-ray detecting unit 5. The X-ray diagnosis apparatus 1 is also provided with an arithmetic and control unit 11, an X-ray control unit 12, an aperture control unit 13, a drive control unit 14, a collected data processing unit 15, a user interface 16, a display data processing unit 17, and a fluoroscopy radiation condition setting unit 18.

User Interface 16

The user interface 16 includes a display unit 161 and an operation unit 162. The display unit 161 is constituted by a display device having an optional form such as a cathode ray tube (CRT) display or a liquid crystal display (LCD). The display unit 161 displays various screens and images under control of the arithmetic and control unit 11.

The operation unit 162 is constituted by operating devices and input devices having an optional form such as a keyboard, a mouse, a trackball, a joystick, a foot pedal, and a control panel. The arithmetic and control unit 11 receives an operation signal output from the operation unit 162 based on a performed operation and executes control or an arithmetic operation corresponding to the content of the operation.

In FIG. 1, the display unit 161 and the operation unit 162 are separated from each other. However, they may be integrally formed as in a touch-panel LCD and a pen tablet.

Couch 2

A subject P is placed on the patient table of the couch 2. The subject P is placed such that the body axis direction thereof is aligned with the longitudinal direction of the patient table of the couch 2. The patient table can move at least in the longitudinal direction of the couch 2 (in the body axis direction of the subject P) by a driving unit (not illustrated) thereof. The patient table may be moved in the short direction, or may be rotationally moved horizontally to the subject.

X-Ray Control Unit 12—Main Control Unit 121

As illustrated in FIG. 1, the X-ray control unit 12 includes a high voltage generating unit 122 that generates a high voltage and a main control unit 121 (microprocessor or the like) that controls the high voltage generating unit. Although the X-ray control unit 12 has other functions, they are not illustrated.

The main control unit 121 receives information of a fluoroscopy radiation condition such as an X-ray condition (tube voltage (kV), tube current (A), irradiation time (s)) set in advance from the fluoroscopy radiation condition setting unit 18 via the arithmetic and control unit 11. The main control unit 121 also receives an X-ray irradiation instruction signal from the operation unit 162 and the like via the arithmetic and control unit 11. Then the main control unit 121 controls each component related to irradiation (output) of the X-rays, such as the high voltage generating unit 122, based on the fluoroscopy radiation condition.

For example, the main control unit 121 generates an instruction signal for finding out the irradiation timing of X-rays based on the X-ray irradiation instruction signal and irradiation time information included in the X-ray condition. The instruction signal allows a voltage to be supplied to the high voltage generating unit 122. The main control unit 121 also receives the fluoroscopy radiation condition (X-ray condition and the like) corresponding to a comparison result by a pixel value comparing unit 154 included in the collected data processing unit 15 to be described later. The main control unit 121 controls the high voltage generating unit 122 and the like based on the adjusted fluoroscopy radiation condition.

When an operator performs an operation to interrupt fluoroscopy imaging through the operation unit 162, a signal for instructing to stop the X-ray irradiation is transmitted from the arithmetic and control unit 11 to the main control unit 121. Upon receiving the signal, the main control unit 121 stops driving of each component related to the irradiation (output) of the X-rays, such as the high voltage generating unit 122, and stops the X-ray irradiation. In addition, upon receiving the signal, the main control unit 121 causes a storage unit (not illustrated) to store therein the fluoroscopy radiation condition corresponding to an LIH image. When a captured image at a time point other than the time when the fluoroscopy is stopped is used as the LIH image, the main control unit 121 causes the storage unit to store therein the fluoroscopy radiation condition at a time point of capturing the image. The fluoroscopy radiation condition corresponding to the LIH image is an example of an "adjusted operating condition".

The fluoroscopy radiation condition corresponding to the LIH image is acquired as follows by way of example. While general fluoroscopy is being continued, the main control unit 121 causes the storage unit to temporarily store therein the fluoroscopy radiation condition. With a configuration in which the fluoroscopy radiation condition is successively updated in a case of the ABC, the parameters of the fluoroscopy radiation stored in the storage unit are updated every time when an instruction for updating is received from the pixel value comparing unit 154 and the like included in the collected data processing unit 15 to be described later. Upon receiving the signal for instructing to stop the X-ray irradiation, the main control unit 121 causes, through the arithmetic and control unit 11, the fluoroscopy radiation condition setting unit 18 to store therein the fluoroscopy radiation condition temporarily stored in the storage unit, as the fluoroscopy radiation condition corresponding to the LIH image, at least until the partial fluoroscopy is started.

Upon receiving an instruction signal for starting the partial fluoroscopy, the main control unit 121 reads out the fluoroscopy radiation condition corresponding to the LIH image from the storage unit (not illustrated). The main control unit 121 sets the fluoroscopy radiation condition as a fluoroscopy radiation condition in the partial fluoroscopy. When the general fluoroscopy is switched to the partial fluoroscopy, the medical diagnostic imaging apparatus according to the embodiment stops the ABC and performs fluoroscopy by fixing the read-out fluoroscopy radiation condition. Described in detail later will be processing in the case in which the partial fluoroscopy is performed with the fluoroscopy radiation condition fixed when the general fluoroscopy is switched to the partial fluoroscopy. In the partial fluoroscopy, the fluoroscopy radiation condition such as the X-ray condition can be changed according to an operation by the operator. In a configuration in which the X-ray condition may be changed by the operator, the display unit 161 may display a warning when an input leading to an increase in the dose of radiation exposure is received.

X-Ray Control Unit 12—High Voltage Generating Unit 122

The main control unit 121 controls the high voltage generating unit 122 to apply a high voltage required for the X-ray irradiation to the X-ray tube 3. To apply the high voltage with the high voltage generating unit 122, a high frequency inverter method may be employed, for example. That is, the high voltage generating unit 122 rectifies an alternating-current power supply of 50/60 Hz into a direct current. The high voltage generating unit 122 converts the direct current into an alternating current having a high frequency of several kilohertz or more to boost the voltage. The high voltage generating unit 122 rectifies again and applies the current. In the fluoroscopy, the X-ray control unit 12 repeats such operations. Accordingly, the imaging is repeated. That is, the main control unit 121 controls the fluoroscopy so as to irradiate the subject with X-ray pulses at predetermined intervals via the high voltage generating unit 122. The fluoroscopic image is generated by the fluoroscopy. The fluoroscopy radiation condition is an example of "an operating condition of an imaging unit".

The X-ray control unit 12 controls the X-ray irradiation under the adjusted fluoroscopy radiation condition according to the ABC by the collected data processing unit 15. The specific content of the control by the collected data processing unit 15 will be described later.

X-Ray Tube 3

The X-ray tube 3 generates X-rays having predetermined intensity upon receiving the application of the high voltage generated by the high voltage generating unit 122. A voltage value or a current value of the high voltage applied to the X-ray tube 3 is set by a user through the user interface 16. Alternatively, these values may be configured to be set automatically.

X-Ray Aperture 4

Figure 2:
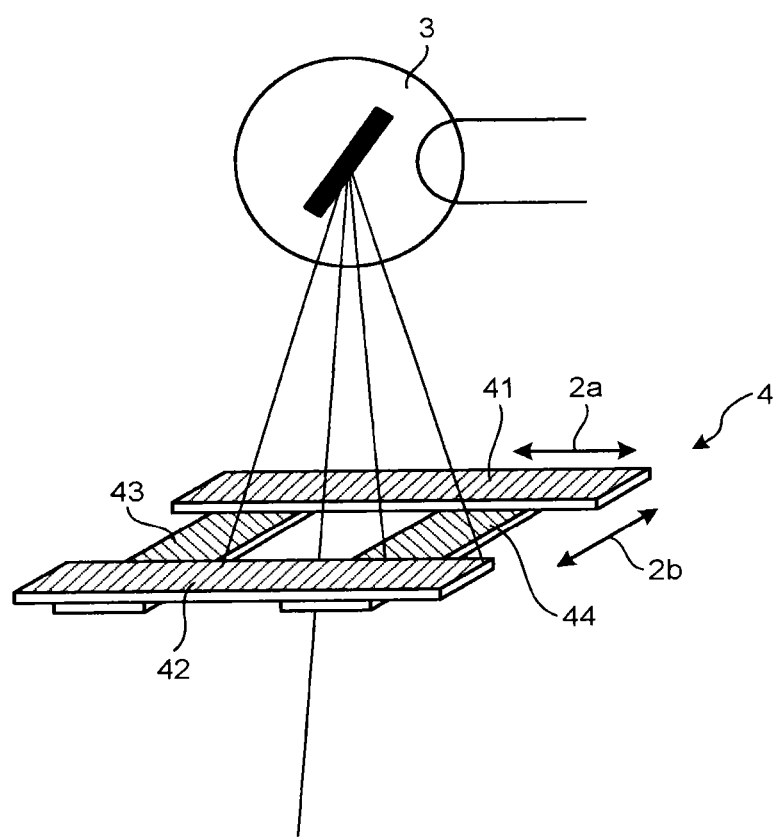
FIG. 2 is a schematic perspective view illustrating an example of the configuration of an X-ray aperture according to the embodiment.

FIG. 2 is a schematic perspective view illustrating an example of the configuration of the X-ray aperture 4. For example, as illustrated in FIG. 2, the X-ray aperture 4 is configured such that plate-like aperture blades 41, 42, 43, and 44 are arranged on all the sides. The aperture blades 41 to 44 are composed by a material that absorbs X-rays, such as tungsten or molybdenum. The aperture blades 41 to 44 are arranged such that each of the end faces thereof is orthogonal to the end face of an adjacent blade. The opening formed by the end faces on the inner sides of the aperture blades 41 to 44 has a rectangular shape.

Aperture Control Unit 13

The aperture control unit 13 functions so as to form an irradiation field in various forms (sizes and shapes) by moving the aperture blades 41 to 44 of the X-ray aperture 4. The aperture control unit 13 is provided with an actuator for driving each of the aperture blades 41 to 44 and a control unit (microprocessor or the like) for controlling the actuator. The aperture control unit 13 performs control for moving the aperture blades 41 and 42 respectively in a short direction 2b (a direction orthogonal to a longitudinal direction 2a) of the couch 2. The aperture control unit 13 also performs control for moving the aperture blades 43 and 44 respectively in the longitudinal direction 2a of the couch 2 (refer to FIG. 2). The control of the X-ray aperture 4 by the aperture control unit 13 is performed based on the positional information of the region of interest received from the fluoroscopy radiation condition setting unit 18.

In this manner, the X-ray passing region F having a substantially quadrangular pyramid shape (refer to FIG. 1) in which the X-ray tube 3 serves as the apex and a detection surface of the X-ray detecting unit 5 serves as the bottom face is formed by the X-ray aperture 4 controlled by the aperture control unit 13. That is, the X-ray irradiation field corresponding to the X-ray passing region F is formed.

The irradiation field means a common area of the X-ray passing region and a plane traversing the X-ray passing region, that is, an area of the plane irradiated with the X-rays. For example, a plane including the longitudinal direction 2a and the short direction 2b and passing through the subject P is the target area of the X-ray irradiation field with respect to the subject P. In addition, a plane including the longitudinal direction 2a and the short direction 2b and passing through the detection surface of the X-ray detecting unit 5 is the target area of the X-ray irradiation, that is, the X-ray irradiation field with respect to the detection surface of the X-ray detecting unit 5.

When an instruction for shifting to the partial fluoroscopy is provided during the fluoroscopy, the aperture control unit 13 narrows the irradiation field. Hereinafter, for the sake of convenience, the fluoroscopy during which a fluoroscopic area is narrowed and that is performed in a region of interest narrower than the fluoroscopic area is simply referred to as "partial fluoroscopy". The region of interest in the partial fluoroscopy is simply referred to as a "region of interest for partial fluoroscopy". A fluoroscopic image generated by the partial fluoroscopy is simply referred to as a "partial fluoroscopic image". The fluoroscopic area is an example of a "first X-ray irradiation area". The region of interest for partial fluoroscopy is an example of a "second X-ray irradiation area".

Figure 3:
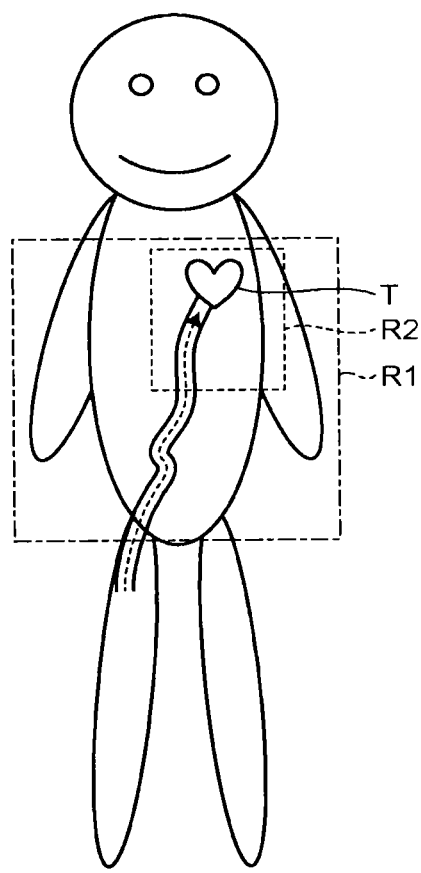
FIG. 3 is a schematic diagram illustrating an example of the relation between a general region of interest and a region of interest for partial fluoroscopy.

With reference to FIG. 3, the partial fluoroscopy and a region of interest for partial fluoroscopy R2 will be described by taking an example in which the fluoroscopy is performed with ablation treatment. FIG. 3 is a schematic diagram illustrating an example of the relation between a general region of interest R1 and the region of interest for partial fluoroscopy R2. In the fluoroscopy during ablation treatment, at a time before and after the insertion of a catheter, an area including the insertion position of the catheter and a target site T (arrhythmia or the like) of the ablation treatment may be set as the general region of interest R1 as illustrated in FIG. 3, for example.

Thereafter, when the catheter moves toward the target site, the operator may instruct to perform the partial fluoroscopy and designate the region of interest for partial fluoroscopy R2 via the operation unit 162. For example, the operator designates a narrower region of interest for partial fluoroscopy including the catheter close to (or at) the target site and the target site. That is, the region of interest for partial fluoroscopy at least overlaps with the region of interest R1 in the LIH (an initial fluoroscopic area or the like), and is designated to be narrower than the region of interest.

Specifically, the operator can set the region of interest (imaging area) with reference to the subject (or the patient table) on a setting screen for the region of interest (for example, refer to FIG. 3) displayed on the display unit 161 by using the operation unit 162. For example, it is assumed that the subject and the patient table are displayed on the setting screen for the region of interest. On the screen, frames (R1, R2, and the like) indicating the regions of interest with respect to the subject are displayed. The frames can be enlarged or contracted by the operator performing an operation of range specification. For example, the operator can operate the frames through the operation unit 162 so that the insertion position of the catheter and the like and a lesion are included in the frames. The operator can perform an operation for defining the region of interest in this manner. The thus defined region of interest is transmitted to the fluoroscopy radiation condition setting unit 18, and set as an imaging area by the fluoroscopy radiation condition setting unit 18.

When the region of interest is set on the setting screen for the region of interest as described above, the fluoroscopy radiation condition setting unit 18 sets, for example, a relative position of the region of interest with respect to the patient table with reference to the coordinate position on the setting screen for the region of interest as the information of the imaging area. The thus set information of the imaging area is transmitted from the fluoroscopy radiation condition setting unit 18 to the aperture control unit 13 via the arithmetic and control unit 11. In a case where the user interface 16 of a touch-panel type is used, the display unit 161 receives a direct input, and the region of interest is set.

When the region of interest for partial fluoroscopy R2 is designated, the aperture control unit 13 moves the aperture blades 41 to 44 of the X-ray aperture 4 respectively so that the irradiation field is an area corresponding to the region of interest for partial fluoroscopy R2.

X-Ray Detecting Unit 5

The X-ray detecting unit 5 detects the X-rays passing through the subject and converts the detection result (hereinafter, referred to as "detection data") into an electric signal. The detection data is output to the collected data processing unit 15 by the X-ray detecting unit 5. As the X-ray detecting unit 5, a flat-type X-ray detecting unit (flat panel detector) or a combination of an image intensifier (I.I.) and a TV camera can be used.

The image intensifier converts the X-rays into light on a fluorescent screen such as a scintillator, and causes photoelectrons to be emitted from a photoelectric surface formed in contact with the fluorescent screen. The image intensifier focuses and accelerates the emitted photoelectrons by an electron lens made of focusing electrodes and anodes, and causes an electron image to be formed on an output fluorescent screen. The image intensifier converts the electron image into a visible image on the output fluorescent screen and captures the visible image by the TV camera. By this imaging, image data (detection data) is obtained.

The flat-type X-ray detecting unit has a detection surface on which multiple rows and columns of X-ray detecting elements are arranged. As the X-ray detecting element, a direct conversion type and the like can be used. With this X-ray detecting element, an electron-hole pair in a semiconductor is generated by the X-rays. Electrical charge data is obtained by utilizing the movement thereof toward the electrodes (that is, a photoconductive phenomenon). The electric charge data output from each of the elements includes the coordinate information of the element in a two-dimensional coordinate system based on a two-dimensional arrangement of the elements.

Figure 4:
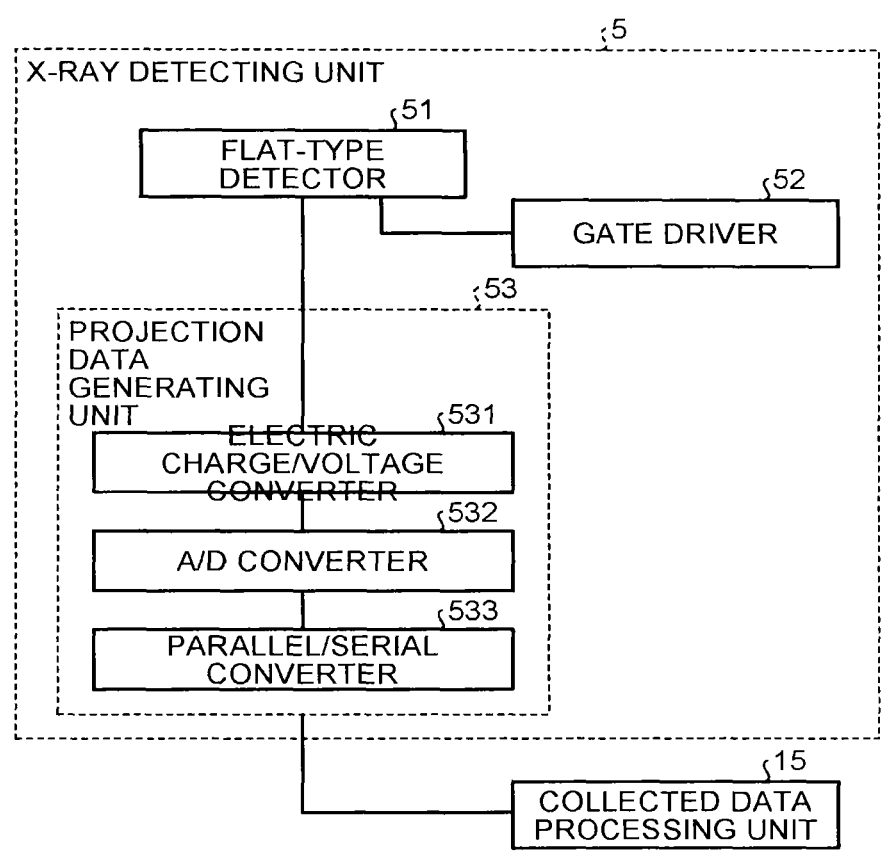
FIG. 4 is a schematic block diagram illustrating an example of the functional configuration of an X-ray detecting unit according to the embodiment.

As an example of the X-ray detecting element of the flat-type X-ray detecting unit, an indirect conversion type that converts transmitted X-rays into electric charge data by a fluorescent material, a photoelectric conversion element, and the like can be used. The flat-type X-ray detecting unit having the X-ray detecting element will be described with reference to FIG. 4. FIG. 4 is a schematic block diagram illustrating an example of the functional configuration of the X-ray detecting unit 5 according to the embodiment. As illustrated in FIG. 4, the X-ray detecting unit 5 includes a flat-type detector 51, a gate driver 52, and a projection data generating unit 53. Among these, the projection data generating unit 53 includes an electric charge/voltage converter 531, an A/D converter 532, and a parallel/serial converter 533.

The detecting elements two-dimensionally arranged in the flat-type detector 51 receive the X-rays passing through the subject P and accumulate signal charges proportional to the amount of the passing X-rays. When the X-ray irradiation is terminated, the gate driver 52 receives a clock pulse from the arithmetic and control unit 11. Upon receiving the clock pulse, the gate driver 52 supplies a drive pulse to a thin film transistor (TFT) and the like of the flat-type detector 51 and sequentially reads out the accumulated signal charges.

The read-out signal charges are transmitted to the electric charge/voltage converter 531 of the projection data generating unit 53. The electric charge/voltage converter 531 converts the signal charge into a voltage. The voltage is converted into a digital signal in the A/D converter 532. Thereafter, the parallel/serial converter 533 converts the digital signal into the projection data of one line. The parallel/serial converter 533 temporarily stores the projection data of one line in a buffer memory. Then the parallel/serial converter 533 serially reads out the projection data stored in the buffer memory thereof in a unit of line, and sequentially stores the projection data in a storage unit 156 of the collected data processing unit 15 to generate two-dimensional projection data. The X-ray detecting unit 5 illustrated in FIG. 4 is an example of the X-ray detecting unit according to the embodiment. Hereinafter, the projection data may be referred to as "detection data".

Moving Unit 6—Drive Control Unit 14

A moving unit 6 enables the X-ray tube 3, the X-ray aperture 4, and the X-ray detecting unit 5 to be integrally moved. The moving unit 6 is driven by the drive control unit 14. The drive control unit 14 includes a drive mechanism for driving the moving unit 6 and a control unit (microprocessor or the like) for controlling operation of the drive mechanism. Hereinafter, the X-ray tube 3, the X-ray aperture 4, and the X-ray detecting unit 5 may be collectively referred to as an "X-ray imaging system". The X-ray imaging system is an example of the "imaging unit".

Collected Data Processing Unit 15

The collected data processing unit 15 forms an image (image data) by performing various image processing and the like on the detection data. The collected data processing unit 15 includes a computer that functions as described above. Details of the collected data processing unit 15 will be described later. The collected data processing unit 15 is an example of functions of an "X-ray image generating unit".

In addition, the collected data processing unit 15 performs the ABC. Only an overview thereof is described herein. For example, the collected data processing unit 15 receives information of the threshold α of the brightness that is set in advance from the fluoroscopy radiation condition setting unit 18. In general fluoroscopy, the collected data processing unit 15 receives a statistic (an average value, an intermediate value, and the like) β of the brightness (pixel value) in the current fluoroscopic image. In addition, the collected data processing unit 15 compares the threshold α with the statistic β. The collected data processing unit 15 causes the comparison result to be reflected in the fluoroscopy radiation condition such as the X-ray condition (tube voltage (kV), tube current (A), and irradiation time (s)) in the X-ray control unit 12. Details of the ABC in the collected data processing unit 15 will be described later. The fluoroscopy radiation condition is an example of the "operating condition of the imaging unit".

Arithmetic and Control Unit 11

The arithmetic and control unit 11 controls each of the components (the X-ray control unit 12, the aperture control unit 13, the drive control unit 14, the collected data processing unit 15, the user interface 16, the fluoroscopy radiation condition setting unit 18, and the like) of the X-ray diagnosis apparatus 1, and executes various arithmetic processing.

For example, the arithmetic and control unit 11 includes a microprocessor such as a central processing unit (CPU), a storage device (memory, hard disk drive, and the like) that stores therein particular computer programs and various data. The microprocessor performs control and arithmetic processing according to the embodiment by executing the computer programs.

Fluoroscopy Radiation Condition Setting Unit 18

The fluoroscopy radiation condition setting unit 18 receives an input from the operation unit 162 via the arithmetic and control unit 11 and sets the X-ray condition, the fluoroscopy radiation condition such as the positional information of the region of interest (ROI), and a detection data collection condition, based on the input. For example, in setting the fluoroscopy radiation condition for the fluoroscopy, the operator sets the tube voltage (kV) according to the body thickness or an imaging site of the subject. According to the setting of the tube voltage (kV), the fluoroscopy radiation condition setting unit 18 sets (stores) the tube current (A) and the irradiation time (s). The set fluoroscopy radiation condition and the set detection data collection condition are transmitted to the X-ray control unit 12 and the aperture control unit 13 via the arithmetic and control unit 11.

The fluoroscopy radiation condition setting unit 18 also receives an input of the threshold α, which is used for the ABC, from the operation unit 162 via the arithmetic and control unit 11. The fluoroscopy radiation condition setting unit 18 stores the threshold α. When the ABC is performed by the X-ray control unit 12, the fluoroscopy radiation condition setting unit 18 transmits the input threshold α to the collected data processing unit 15 via the arithmetic and control unit 11. The threshold α may be set in advance in the fluoroscopy radiation condition setting unit 18, or may be set depending on the execution of the fluoroscopy. The threshold α is a threshold corresponding to the statistic of the pixel value of the X-ray image calculated by a pixel value arithmetic unit 153 (to be described later) in the X-ray control unit 12. The statistic of the pixel value is exemplified by an average value, an intermediate value, a standard deviation, the minimum value, and the maximum value, of the pixel value. The threshold is set according to a calculation method of the statistic. Specific contents of the ABC will be described later. The fluoroscopy radiation condition setting unit 18 functions as an example of the "storage unit".

The fluoroscopy radiation condition setting unit 18 receives information of the general region of interest R1 and the region of interest for partial fluoroscopy R2 from the operation unit 162 via the arithmetic and control unit 11. For example, on a setting screen for the fluoroscopy radiation condition as illustrated in FIG. 3, when the operator performs an operation to set the general region of interest R1 and the region of interest for partial fluoroscopy R2, the positional information of the regions of interest is received from the operation unit 162 via the arithmetic and control unit 11. The positional information is set as a fluoroscopic area by the fluoroscopy radiation condition setting unit 18.

The entire configuration of the X-ray diagnosis apparatus 1 according to the first embodiment has been described so far. Under such a configuration, in the X-ray diagnosis apparatus 1 according to the first embodiment, when the general fluoroscopy is switched to the partial fluoroscopy through the processing of the collected data processing unit 15 and the display data processing unit 17 to be described in detail below, the partial fluoroscopy is performed under the fluoroscopy radiation condition of the general fluoroscopy to enable the prevention of an increase in the dose of radiation exposure of the subject in the X-ray imaging. Herein, with reference to FIG. 5, described will be a case where the dose of radiation exposure is increased through the ABC when the general fluoroscopy is switched to the partial fluoroscopy.

FIG. 5 is a diagram for explaining a problem according to the related art. FIG. 5 illustrates a state in which X-rays are delivered from the X-ray tube 3 to the subject P, viewed along the body axis direction. In FIG. 5, (A) illustrates a state of the X-ray aperture 4 in general fluoroscopy, and (B) illustrates a state of the X-ray aperture 4 in partial fluoroscopy. For example, when X-rays are delivered from the X-ray tube 3 to the subject P, the X-rays are delivered toward the X-ray detecting unit 5 from the X-ray tube 3, as illustrated in (A) of FIG. 5. As illustrated in (A) of FIG. 5, the X-rays delivered from the X-ray tube 3 become a transmitted X-ray 61 that pass through the subject P and a scattered radiation 62 that is reflected due to an influence of a structure in the subject P.

In such a case, for example, as illustrated in (A) of FIG. 5, a detecting element 5a of the X-ray detecting unit 5 detects the transmitted X-ray 61 and the scattered radiation 62. As a result, in the case of general fluoroscopy, an image corresponding to the detecting element 5a is generated based on the transmitted X-ray 61 and the scattered radiation 62. On the other hand, in a case where the general fluoroscopy is switched to the partial fluoroscopy, the X-ray aperture 4 is narrowed down and the X-ray irradiation field is narrowed as illustrated in (B) of FIG. 5. That is, as illustrated in (B) of FIG. 5, the X-rays that would be reflected as the scattered radiation 62 are absorbed by the X-ray aperture and do not reach the subject P. As a result, in the case of partial fluoroscopy, an image corresponding to the detecting element 5a is generated based on the transmitted X-ray 61.

When the general fluoroscopy is switched to the partial fluoroscopy as described above, the scattered radiation 62 incident on the detecting element 5a reduces so that the brightness level of the partial fluoroscopic image reduces compared to the LIH image. When the ABC is in operation, the fluoroscopy radiation condition is changed to adjust the reduced brightness level. As an example, when the brightness level of a particular region in the general fluoroscopy is "400" and "100" of "400" is an increase due to the scattered radiation 62, and the threshold of the ABC is "400", the brightness level of the particular region in the partial fluoroscopy is "300", which does not include the scattered radiation 62, so that the fluoroscopy radiation condition is changed to adjust the brightness level to "400". That is, the dose of X-rays delivered from the X-ray tube 3 is increased, so that the dose of radiation exposure at a position through which the X-rays pass in the subject is increased. The X-ray diagnosis apparatus 1 according to the first embodiment thus performs the partial fluoroscopy under the fluoroscopy radiation condition of general fluoroscopy to prevent the dose of radiation exposure of the subject from increasing in the X-ray imaging.

Configuration of Collected Data Processing Unit 15

Figure 6:
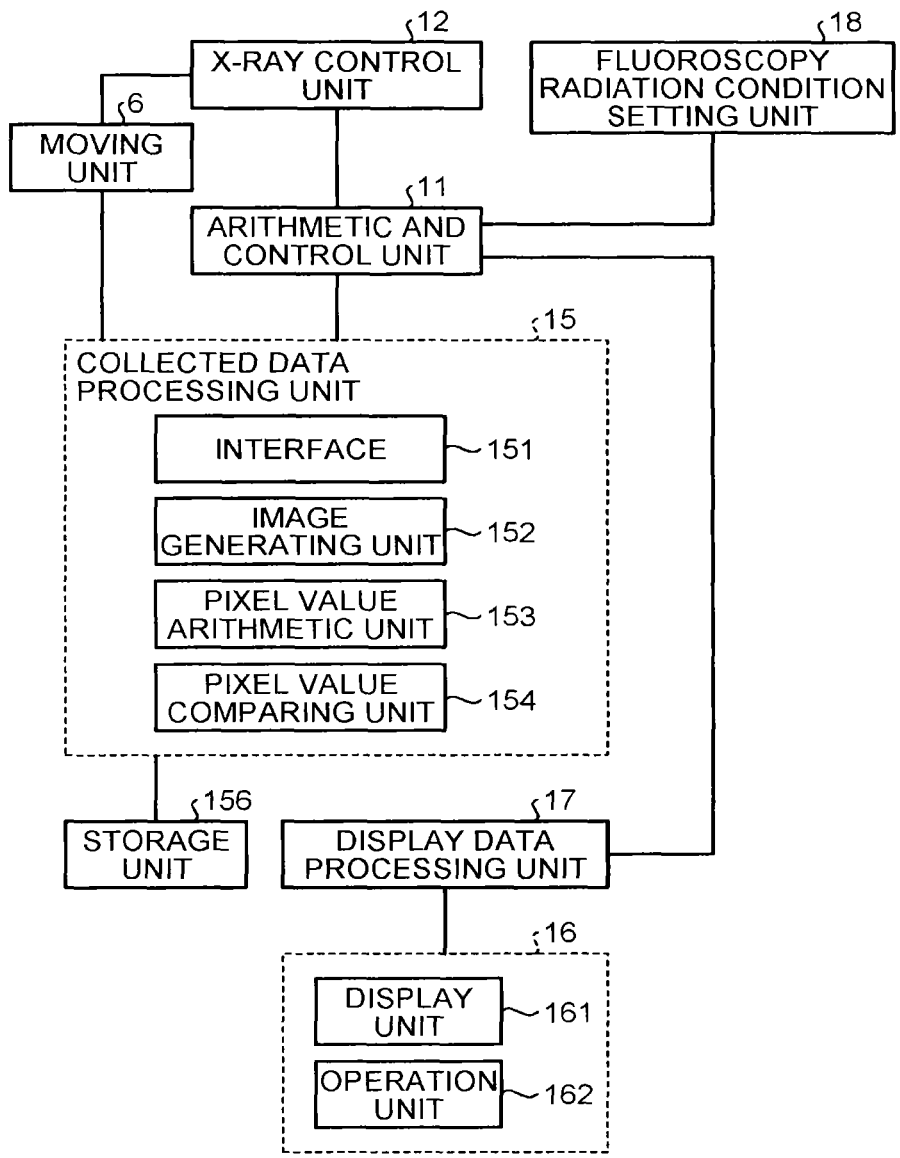
FIG. 6 is a schematic block diagram illustrating part of the functional configuration of a collected data processing unit according to a first embodiment.

The configuration of the collected data processing unit 15 in the X-ray diagnosis apparatus will be described with reference to FIG. 6. FIG. 6 is a schematic block diagram illustrating part of the functional configuration of the collected data processing unit 15 according to the first embodiment. The collected data processing unit 15 forms an image (image data) by performing various image processing and the like on the detection data. The collected data processing unit 15 also performs the ABC and transmits the fluoroscopy radiation condition based on the processing result to the X-ray control unit 12. The collected data processing unit 15 is an example of an "adjusting unit". The collected data processing unit 15 is also an example of the "control unit" together with the X-ray control unit 12.

As illustrated in FIG. 6, the collected data processing unit 15 includes an interface 151, an image generating unit 152, the pixel value arithmetic unit 153, and a pixel value comparing unit 154.

Interface 151

As illustrated in FIG. 1, the collected data processing unit 15 is connected to the X-ray detecting unit 5. The interface 151 receives detection data from the X-ray detecting unit 5. The detection data received via the interface 151 is stored in the storage unit 156.

Image Generating Unit 152

The image generating unit 152 generates an X-ray image based on the detection data. The image generating unit 152 generates two-dimensional image data based on the detection data, for example. The image generating unit 152 may perform reconstruction based on the two-dimensional detection data of multiple frames, generate volume data, and cause the storage unit 156 to store therein the volume data. In a case where the detection data is sequentially transmitted from the X-ray detecting unit 5 through the fluoroscopy, the image generating unit 152 sequentially generates fluoroscopic images in response to the reception of the detection data.

When the operator performs the operation to interrupt (stop) the fluoroscopy through the operation unit 162 in a situation where the fluoroscopy is performed by the X-ray imaging system, the signal for instructing to stop the X-ray irradiation is transmitted to the X-ray control unit 12. At this timing, an instruction for storing the LIH image is transmitted from the arithmetic and control unit 11 to the collected data processing unit 15. Upon receiving the instruction for storing, the image generating unit 152 causes the storage unit 156 to store therein the LIH image based on the fluoroscopic image. For example, if there is an instruction for interrupting the fluoroscopy via the operation unit 162, the image generating unit 152 specifies the last frame (detection data) of the fluoroscopic image received from the X-ray detecting unit 5 and stored in the storage unit 156. The image generating unit 152 causes the storage unit 156 to store therein a generated image, that is, the LIH image in addition to the fluoroscopic image to be displayed on the display unit 161, based on the last flame.

However, the image generating unit 152 may not necessarily cause the storage unit 156 to store therein the last frame of the fluoroscopic image. For example, when there is an instruction for storing an image from the operation unit 162 while the fluoroscopy is performed by the X-ray imaging system, the image generating unit 152 causes the storage unit 156 to store therein a generated X-ray image (herein, a captured image/a static image). Hereinafter, for the sake of convenience, both an image based on the last frame of the fluoroscopic image and an image based on a frame according to an instruction for storing an image by the operator may be referred to as an "LIH image". An LIH image is an example of a "first X-ray image".

Pixel Value Arithmetic Unit 153

The pixel value arithmetic unit 153 calculates a statistic $\beta$ of a pixel value in an X-ray image such as a fluoroscopic image. The statistic $\beta$ may be, for example, an average value, an intermediate value, a standard deviation, the minimum value, and the maximum value, of the pixel value. The pixel value arithmetic unit 153 receives data of the X-ray image generated by the image generating unit 152 via the arithmetic and control unit 11. The pixel value arithmetic unit 153 calculates the statistic $\beta$ for part or all of the pixels in a fluoroscopic image. For example, the pixel value arithmetic unit 153 calculates the average value of the pixel value of an X-ray image. The pixel value arithmetic unit 153 transmits information of the obtained statistic $\beta$ to the pixel value comparing unit 154. In the fluoroscopy, the pixel value arithmetic unit 153 repeats the above steps.

Pixel Value Comparing Unit 154

The pixel value comparing unit 154 receives the information of the threshold $\alpha$ of the pixel value from the fluoroscopy radiation condition setting unit 18 via the arithmetic and control unit 11, the interface 151, and the like. The pixel value comparing unit 154 receives the information of the statistic $\beta$ of the pixel value obtained by the pixel value arithmetic unit 153, and compares it with the threshold $\alpha$. The pixel value comparing unit 154 adjusts the fluoroscopy radiation condition based on the comparison result. As an example of the adjustment, when "$\alpha$=300" and $\beta$=200", "300/200" is reflected in the condition set in advance in the fluoroscopy radiation condition setting unit 18.

The pixel value comparing unit 154 may be configured to simply transmit the comparison result to the main control unit 121. In this case, the pixel value comparing unit 154 firstly transmits the obtained comparison result to the main control unit 121. Similarly to the processing of the pixel value comparing unit 154, the main control unit 121 adjusts the fluoroscopy radiation condition based on the comparison result. The comparison result described herein may be, for example, information indicating a difference between the threshold $\alpha$ and the statistic $\beta$ of the pixel value or information indicating a ratio thereof.

In addition, the pixel value comparing unit 154 may determine whether the comparison result is within a predetermined range. That is, the pixel value comparing unit 154 determines whether the difference or the ratio between the threshold α and the statistic β of the pixel value obtained by the pixel value arithmetic unit 153 is within a predetermined range. Accordingly, the pixel value comparing unit 154 determines whether the pixel value (brightness) of the fluoroscopic image is within a range set in advance. In this example, if the difference or the like is within the predetermined range, the pixel value comparing unit 154 determines that the fluoroscopy radiation condition does not need to be changed, and does not transmit the comparison result to the main control unit 121. If the difference is out of the predetermined range, the comparison result, which is the difference, is transmitted to the main control unit 121. The main control unit 121 adjusts the fluoroscopy radiation condition according to the difference and the like.

The embodiment is not limited to the configuration in which the main control unit 121 receives the comparison result from the pixel value comparing unit 154 and adjusts the fluoroscopy radiation condition. The pixel value comparing unit 154 may adjust the fluoroscopy radiation condition based on the comparison result. In this example, the pixel value comparing unit 154 transmits the adjusted fluoroscopy radiation condition to the main control unit 121. The main control unit 121 performs control related to the fluoroscopy radiation based on the adjusted fluoroscopy radiation condition received from the pixel value comparing unit 154.

When the general fluoroscopy is switched to the partial fluoroscopy, the pixel value comparing unit 154 according to the first embodiment performs control for executing the partial fluoroscopy under the fluoroscopy radiation condition of the general fluoroscopy irrespective of the comparison result between the threshold α and the statistic β of the pixel value. For example, the pixel value comparing unit 154 determines a case in which an operation for designating the region of interest for partial fluoroscopy R2 is received via the operation unit 162 as a switching to the partial fluoroscopy, and stops the adjustment of the fluoroscopy radiation condition for the fluoroscopy radiation condition setting unit 18. Accordingly, the main control unit 121 included in the X-ray control unit 12 causes the partial fluoroscopy to be executed under the fluoroscopy radiation condition of the general fluoroscopy (fluoroscopy radiation condition corresponding to the LIH image) stored in a storage unit (not illustrated). The control of the fluoroscopy radiation condition at the time of partial fluoroscopy is not limited to the example described above. For example, the pixel value comparing unit 154 may control the main control unit 121, via the arithmetic and control unit 11, to execute the partial fluoroscopy under the fluoroscopy radiation condition at the time of general fluoroscopy.

Storage Unit 156

As described above, the storage unit 156 stores therein the two-dimensional detection data received via the interface 151. In addition, the storage unit 156 stores therein respective X-ray images used for synthetic images such as the LIH image and an angiographic image. The storage unit 156 also stores therein the volume data. The detection data and the X-ray image may be continuously stored in the storage unit 156 and be optionally readable according to an operation by the operator. The detection data and the X-ray image may be temporarily stored in the storage unit 156. Data to be stored may be either a dynamic image or a static image.

As described above, in the first embodiment, when the general fluoroscopy is switched to the partial fluoroscopy, the partial fluoroscopy is executed under the fluoroscopy radiation condition of the general fluoroscopy irrespective of the comparison result between the threshold α and the statistic β of the pixel value. That is, the ABC is off in the partial fluoroscopy. However, the ABC is on in the general fluoroscopy and, for example, controls as described below are performed.

In such a case, the collected data processing unit 15 adjusts the fluoroscopy radiation condition to change a brightness value based on the pixel value of the fluoroscopic image, as the ABC. That is, the collected data processing unit 15 calculates the statistic β of the pixel value (brightness value) for each of the pixels in the fluoroscopic image (the pixel value arithmetic unit 153). The collected data processing unit 15 receives information of the threshold α of the pixel value of the fluoroscopic image stored in the fluoroscopy radiation condition setting unit 18. The X-ray control unit 12 compares the threshold α with the statistic β (pixel value comparing unit 154). As a result of the comparison, if the statistic β does not correspond to the threshold α, the collected data processing unit 15 changes the fluoroscopy radiation condition. For example, if the brightness value of the fluoroscopic image is smaller than the threshold, the fluoroscopy radiation condition is enhanced.

Operation

Figure 7:
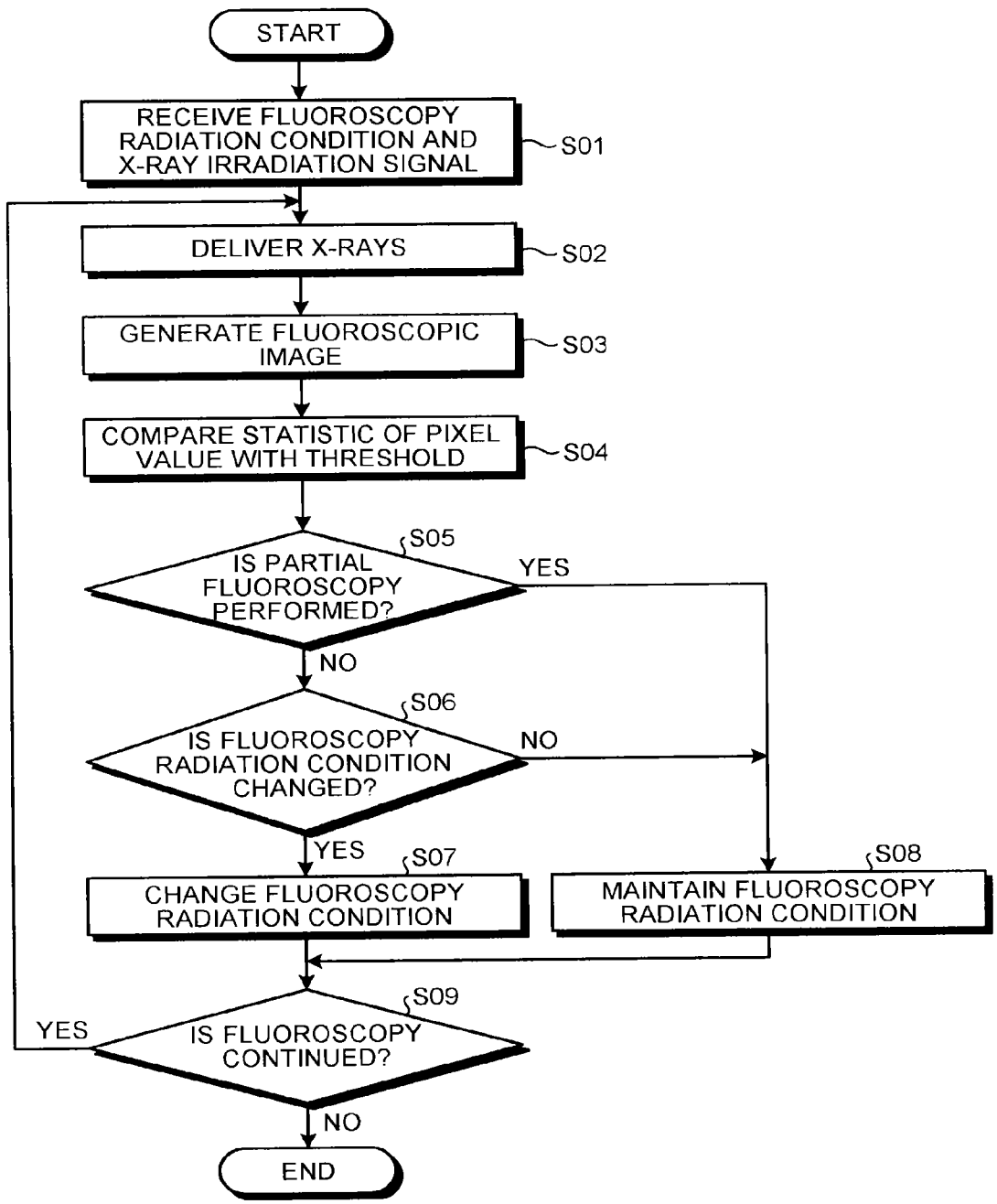
FIG. 7 is a schematic flow chart for explaining the flow of ABC in an X-ray diagnosis apparatus that executes fluoroscopy.

With reference to a flow chart in FIG. 7, an operation of the collected data processing unit 15 in the ABC will be described with an example of the fluoroscopy in the general region of interest R1. FIG. 7 is a schematic flow chart for explaining a flow of the ABC in the X-ray diagnosis apparatus that executes the fluoroscopy.

S01

The main control unit 121 in the X-ray control unit 12 receives the fluoroscopy radiation condition (X-ray condition and the like) set in advance from the fluoroscopy radiation condition setting unit 18. When the operator instructs to start the fluoroscopy in the general region of interest R1 or the region of interest for partial fluoroscopy R2 through the operation unit 162, the X-ray irradiation instruction signal is transmitted to the main control unit 121 via the arithmetic and control unit 11.

S02

The main control unit 121 controls the high voltage generating unit 122 and the like to cause a voltage to be applied to the X-ray tube 3 based on the fluoroscopy radiation condition received from the fluoroscopy radiation condition setting unit 18. The aperture control unit 13 moves the X-ray aperture 4 based on the positional information of the general region of interest R1 received from the fluoroscopy radiation condition setting unit 18, thereby forming the irradiation field. As a result of these operations, the X-rays are delivered in the formed irradiation field.

S03

When the X-ray detecting unit 5 generates detection data based on the transmitted X-ray, the detection data is transmitted to the collected data processing unit 15. Upon receiving the detection data via the interface 151, the collected data processing unit 15 temporarily stores the detection data in the storage unit 156. The image generating unit 152 reads out the detection data from the storage unit 156 and executes predetermined processing on the detection data. The image generating unit 152 then generates a fluoroscopic image and causes the display unit 161 to display the fluoroscopic image.

S04

The collected data processing unit 15 receives the data of the fluoroscopic image from the storage unit 156. The pixel value arithmetic unit 153 calculates the statistics β (average value and the like) of the pixel values of part or the entire fluoroscopic image received from the storage unit 156. The pixel value comparing unit 154 compares the statistic β of the pixel value obtained by the pixel value arithmetic unit 153 with the threshold α received from the fluoroscopy radiation condition setting unit 18. The pixel value comparing unit 154 may determine whether the comparison result is within a predetermined range.

S05

The pixel value comparing unit 154 determines whether the fluoroscopy that is instructed to be started is the partial fluoroscopy. If it is determined that the fluoroscopy is not the partial fluoroscopy, that is, the fluoroscopy is the general fluoroscopy (No at S05), the process proceeds to S06 and the pixel value comparing unit 154 determines whether to change the fluoroscopy radiation condition. If it is determined that the fluoroscopy is the partial fluoroscopy (Yes at S05), the process proceeds to S08 and the pixel value comparing unit 154 maintains the fluoroscopy radiation condition. That is, the pixel value comparing unit 154 performs control for executing the partial fluoroscopy under the fluoroscopy radiation condition of the general fluoroscopy.

S06

The pixel value comparing unit 154 (or the main control unit 121) compares the threshold α with the statistic β. The pixel value comparing unit 154 determines whether to change the fluoroscopy radiation condition such as the X-ray condition based on the comparison result.

S07

If a difference between the statistic β of the pixel value and the threshold α is large as a result of the comparison by the pixel value comparing unit 154 (Yes at S06), the pixel value comparing unit 154 (or the main control unit 121) adjusts (changes) parameters related to the tube voltage (kV), the tube current (A), and the irradiation time (s). The main control unit 121 controls the high voltage generating unit 122 according to the adjusted fluoroscopy radiation condition.

S08

If the fluoroscopy that is instructed to be started is the partial fluoroscopy (Yes at S05) or if the difference between the statistic β of the pixel value and the threshold α is small (No at S06), the pixel value comparing unit 154 (or the main control unit 121) maintains the fluoroscopy radiation condition as it is.

S09

The pixel value comparing unit 154 (or the main control unit 121) determines whether to continue the fluoroscopy. For example, when the operator instructs to stop the fluoroscopy via the operation unit 162, an instruction signal for stopping the X-ray irradiation is transmitted to the main control unit 121 via the arithmetic and control unit 11. The main control unit 121 sequentially repeats the operations of S02 to S07 until receiving the instruction signal for stopping the X-ray irradiation. The processing of S08 has been described as post-processing of S06 or S07 for the sake of convenience. However, if the main control unit 121 receives the instruction signal for stopping the X-ray irradiation at any of S02 to S05, the main control unit 121 stops the irradiation of the X-ray at that point.

As an example, when the operation to stop the X-ray irradiation (to stop the fluoroscopy) is performed, the main control unit 121 stops the X-ray irradiation by stopping driving each component related to the X-ray irradiation (output) such as the high voltage generating unit 122. According to the operation for instructing to stop, the image generating unit 152 causes the storage unit 156 to store therein the LIH image. The main control unit 121 causes a storage unit (not illustrated) to store therein the fluoroscopy radiation condition corresponding to the LIH image.

Configuration of Display Data Processing Unit 17

Figure 8:
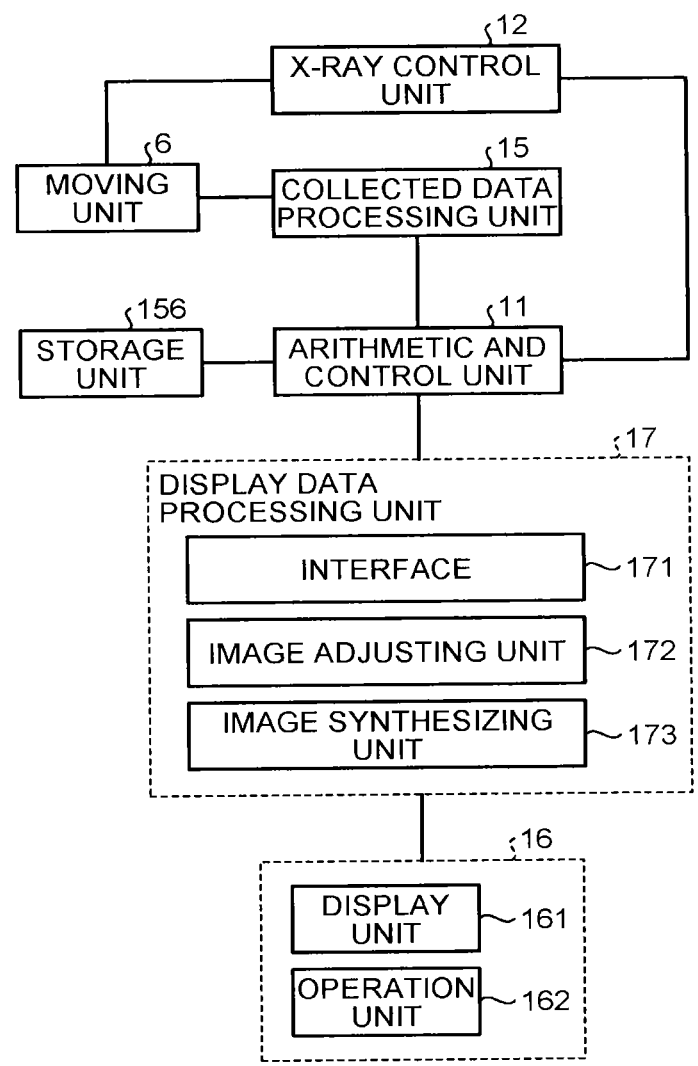
FIG. 8 is a schematic block diagram illustrating a display data processing unit according to the first embodiment.

Next, the configuration of the display data processing unit 17 in the X-ray diagnosis apparatus will be described with reference to FIG. 8. FIG. 8 is a schematic block diagram illustrating part of the functional configuration of the display data processing unit 17 according to the embodiment. The display data processing unit 17 performs various image processing on image data generated by the collected data processing unit 15 to form an image. As illustrated in FIG. 8, the display data processing unit 17 includes an interface 171, an image adjusting unit 172, and an image synthesizing unit 173.

Interface 171

As illustrated in FIG. 8, the display data processing unit 17 is connected to the arithmetic and control unit 11. The interface 171 receives the image data of the X-ray image from the collected data processing unit 15 via the arithmetic and control unit 11. The image data received via the interface 171 is temporarily stored in the storage unit 156.

Image Adjusting Unit 172

The image adjusting unit 172 receives the image data from the collected data processing unit 15 or the storage unit 156 and performs image processing. The image adjusting unit 172 performs image processing such as sharpening of the image, noise reduction, improvement in S/N ratio, edge detection, edge enhancement, and the like. The image adjusting unit 172 has functions such as what are called a spatial filter, a spatial frequency filter, and a time filter. The spatial filter and the spatial frequency filter are exemplified by a filter that performs data smoothing, and a filter that performs edge detection. The filter that performs data smoothing is exemplified by an averaging filter, a weighted averaging filter, a Gaussian filter, and a median filter.

The image adjusting unit 172 includes any filters such as a Sobel filter that performs edge detection, a Prewitt filter, a Roberts filter, and a Laplacian filter. The image adjusting unit 172 may have functions such as image integration processing and recursive filtering as what is called a time filter. The image adjusting unit 172 may also include functions such as low-pass filtering, high-pass filtering, band-pass filtering, band-elimination filtering, and all-pass filtering.

The image adjusting unit 172 performs the filtering (high frequency emphasis and the like) or an affine transformation (image magnification, movement, and the like) on the detection data or the X-ray image. For example, in a case where the image generating unit 152 generates a digital angiographic image, the image adjusting unit 172 performs these pieces of processing on the detection data. The image adjusting unit 172 may emphasize a high-frequency component by unsharp masking.

Image Synthesizing Unit 173

The image synthesizing unit 173 synthesizes (laminates) a plurality of X-ray images and generates a synthesized X-ray image corresponding to an image to be displayed. Hereinafter, the synthesized X-ray image may simply be referred to as a "synthetic image". For example, the image synthesizing unit 173 synthesizes the LIH image and a partial fluoroscopic image to be described later. As another example, the image synthesizing unit 173 synthesizes a road map image based on the volume data and the fluoroscopic image.

In a case where a synthetic image of the LIH image and the partial fluoroscopic image is generated by the image synthesizing unit 173, the LIH image and the partial fluoroscopic image are aligned and synthesized based on the information of operation for designating the region of interest for partial fluoroscopy R2. That is, the region of interest for partial fluoroscopy R2 is set so as to at least overlap with the region of interest R1 (the initial fluoroscopic area or the like) in the LIH image. The position of the region of interest for partial fluoroscopy R2 can be thus indicated by coordinates in the LIH image. Accordingly, the image synthesizing unit 173 receives the positional information of the stored region of interest for partial fluoroscopy R2, and synthesizes the partial fluoroscopic image and the LIH image such that the partial fluoroscopic image is laminated to the LIH image based on the positional information and the coordinates in the LIH image.

When the synthetic image of the LIH image and the partial fluoroscopic image is generated by the image synthesizing unit 173, a synthesis ratio of respective images may be optionally set. However, the synthesis ratio of the partial fluoroscopic image is set such that the partial fluoroscopic image can be at least recognized in the synthetic image. The image synthesizing unit 173 is an example of a "synthesizing unit".

Partial Fluoroscopy

Figure 9:
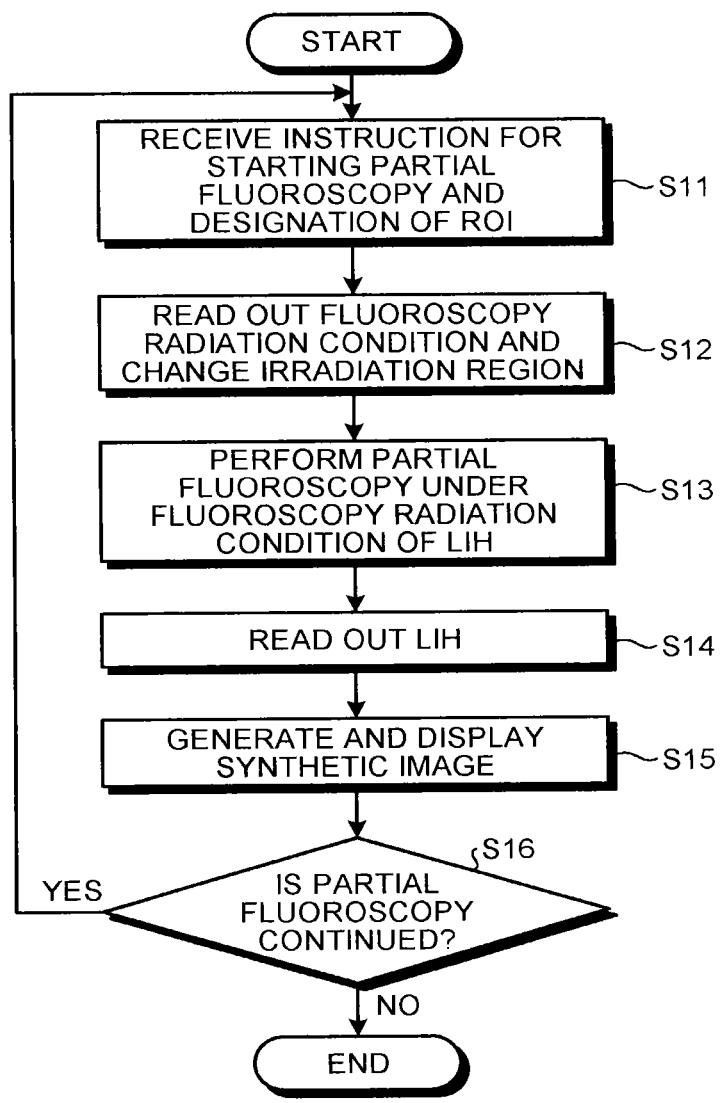
FIG. 9 is a schematic flow chart for explaining the flow of control in an X-ray diagnosis apparatus for partial fluoroscopy.

Next, the control by the X-ray control unit 12 for the partial fluoroscopy and the process flow of the collected data processing unit 15 will be described with reference to FIG. 9. FIG. 9 is a schematic flow chart for explaining the flow of control in a medical diagnostic imaging apparatus for the partial fluoroscopy. As described above, when the operator interrupts the fluoroscopy through the operation unit 162 in a situation where the fluoroscopy is performed in the general region of interest R1 by the X-ray imaging system, the signal for instructing to stop the X-ray irradiation is transmitted to the X-ray control unit 12. If the operator performs an operation for starting the partial fluoroscopy and designates the region of interest for partial fluoroscopy R2 through the operation unit 162, the X-ray control unit 12 performs control in the partial fluoroscopy.

S11

If the operator performs an operation for starting the partial fluoroscopy and designates the region of interest for partial fluoroscopy R2 through the operation unit 162, the positional information of the region of interest for partial fluoroscopy R2 is transmitted to the aperture control unit 13. In contrast, the instruction for starting the partial fluoroscopy is transmitted to the X-ray control unit 12.

S12

The aperture control unit 13 moves each of the aperture blades 41 to 44 of the X-ray aperture 4 based on the positional information of the region of interest for partial fluoroscopy R2. The movement of the aperture blades 41 to 44 limits the X-ray irradiation field to a range corresponding to the region of interest for partial fluoroscopy R2. The X-ray control unit 12 reads out the fluoroscopy radiation condition corresponding to the LIH image from a storage unit (not illustrated).

S13

The main control unit 121 of the X-ray control unit 12 controls the X-ray irradiation field, the high voltage generating unit 122, and the like to perform the X-ray irradiation (partial fluoroscopy) based on the read-out fluoroscopy radiation condition of the LIH image. The irradiation field of the X-ray delivered to the subject from the X-ray tube 3 is limited by the X-ray aperture 4.

S14

When the partial fluoroscopy is started, the image synthesizing unit 173 reads out the LIH image from the storage unit 156.

S15

The image synthesizing unit 173 receives the partial fluoroscopic image generated by the image generating unit 152 and synthesizes it with the LIH image read out at S14. The read-out processing of the LIH image is not limited to a case of the post-processing of S13, and may be performed after S11 until the partial fluoroscopic image is generated.

S16

The main control unit 121 determines whether to continue the partial fluoroscopy. For example, according to an instruction for stopping the fluoroscopy, an instruction signal for stopping the X-ray irradiation is transmitted to the main control unit 121 via the arithmetic and control unit 11. The main control unit 121 sequentially repeats operations of S13 to S15 until receiving the instruction signal for stopping the X-ray irradiation. The processing at S16 is described as post-processing of S15 for the sake of convenience. However, if the main control unit 121 receives the instruction signal for stopping the X-ray irradiation at any of S13 to S15, the main control unit 121 stops the X-ray irradiation at that time point.

Action and Effect

The action and effect of the medical diagnostic imaging apparatus according to the embodiment described above will be described.

The medical diagnostic imaging apparatus according to the embodiment performs the ABC in the general fluoroscopy to adjust the fluoroscopy radiation condition for an optimal pixel value, and performs imaging in the partial fluoroscopy with the fluoroscopy radiation condition fixed to the condition at the time of acquiring the LIH image. That is, in the partial fluoroscopy, the ABC with respect to the X-ray condition is not performed irrespective of the pixel value (brightness) of the partial fluoroscopic image. This can prevent an increase in the dose of radiation exposure of the subject in the partial fluoroscopy. Because the ABC is performed in the general fluoroscopy, the fluoroscopy radiation condition is adjusted in the partial fluoroscopy as well. Accordingly, it is possible to avoid a situation in which a structure in the subject cannot be visually recognized in the partial fluoroscopic image.

First Modification

Next, a first modification of the medical diagnostic imaging apparatus according to the first embodiment will be described. The medical diagnostic imaging apparatus according to the first embodiment performs the ABC based on the brightness of the X-ray image generated by the image generating unit 152. However, the embodiment is not limited thereto, and the ABC may be performed based on the detection data.

Second Modification

In the medical diagnostic imaging apparatus according to the first embodiment, the collected data processing unit 15 is configured to compare the statistic of the pixel value with the threshold. However, the embodiment is not limited thereto. For example, the X-ray control unit 12 may be configured to compare each pixel of the X-ray image with the threshold, and then compare the average value of the comparison result with the threshold. In this example, the first threshold for comparison with each pixel and the second threshold for comparison with the average value may be separately set.

The same effect as those in the above-described embodiment can be achieved by the configuration of the X-ray diagnosis apparatus according to the first modification and the second modification described above.

Second Embodiment

In the first embodiment described above, when the general fluoroscopy is switched to the partial fluoroscopy, an increase in the dose of radiation exposure of the subject in the X-ray imaging is prevented by performing the partial fluoroscopy under the fluoroscopy radiation condition of the general fluoroscopy. The second embodiment will describe a case where the partial fluoroscopy is performed under the fluoroscopy radiation condition of the general fluoroscopy and the display gain of the partial fluoroscopic image is adjusted.

That is, as described above, when the partial fluoroscopy is performed under the fluoroscopy radiation condition of the general fluoroscopy, the brightness level in the partial fluoroscopic image may be decreased compared to the fluoroscopic image of the general fluoroscopy. The X-ray diagnosis apparatus according to the second embodiment thus performs the partial fluoroscopy under the fluoroscopy radiation condition of the general fluoroscopy to prevent an increase in the dose of radiation exposure, and adjust the display gain of the partial fluoroscopic image to cause the brightness level of the partial fluoroscopic image to be similar to the brightness level of the fluoroscopic image of the general fluoroscopy.

Figure 10:
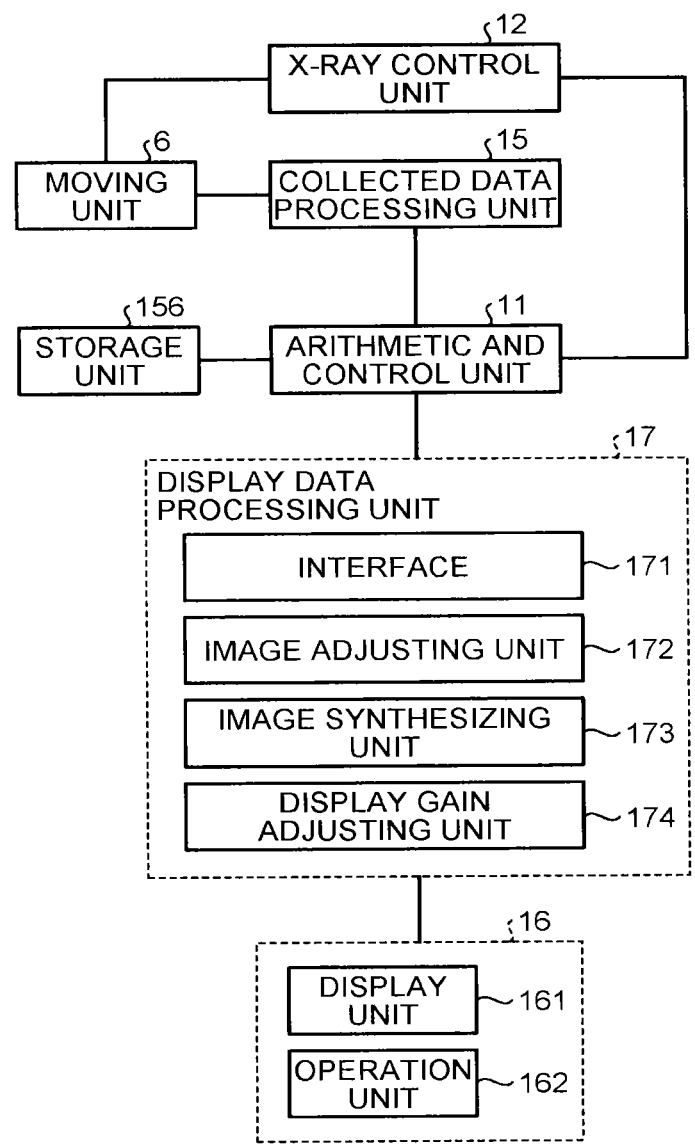
FIG. 10 is a schematic block diagram illustrating part of the functional configuration of a display data processing unit according to a second embodiment.
Figure 11:
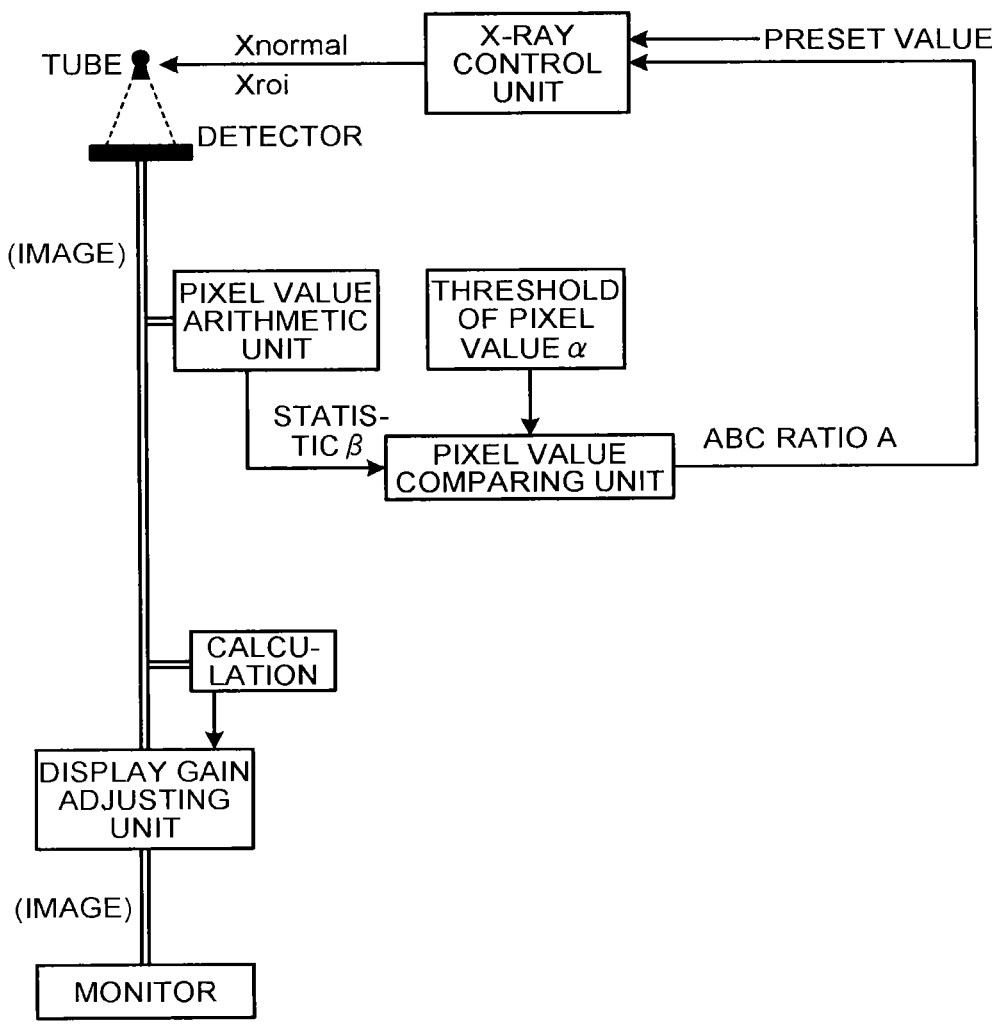
FIG. 11 is a diagram for explaining an example of processing in an X-ray diagnosis apparatus according to the second embodiment.
Figure 12:
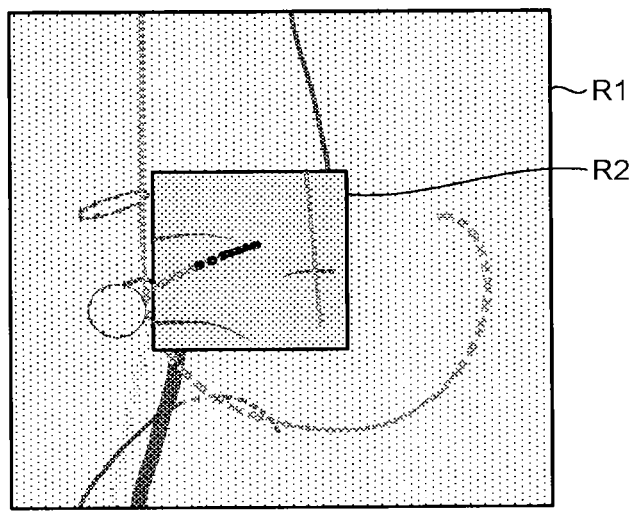
FIG. 12 is a diagram illustrating an example of a partial fluoroscopic image generated by the X-ray diagnosis apparatus according to the second embodiment.
Figure 13:
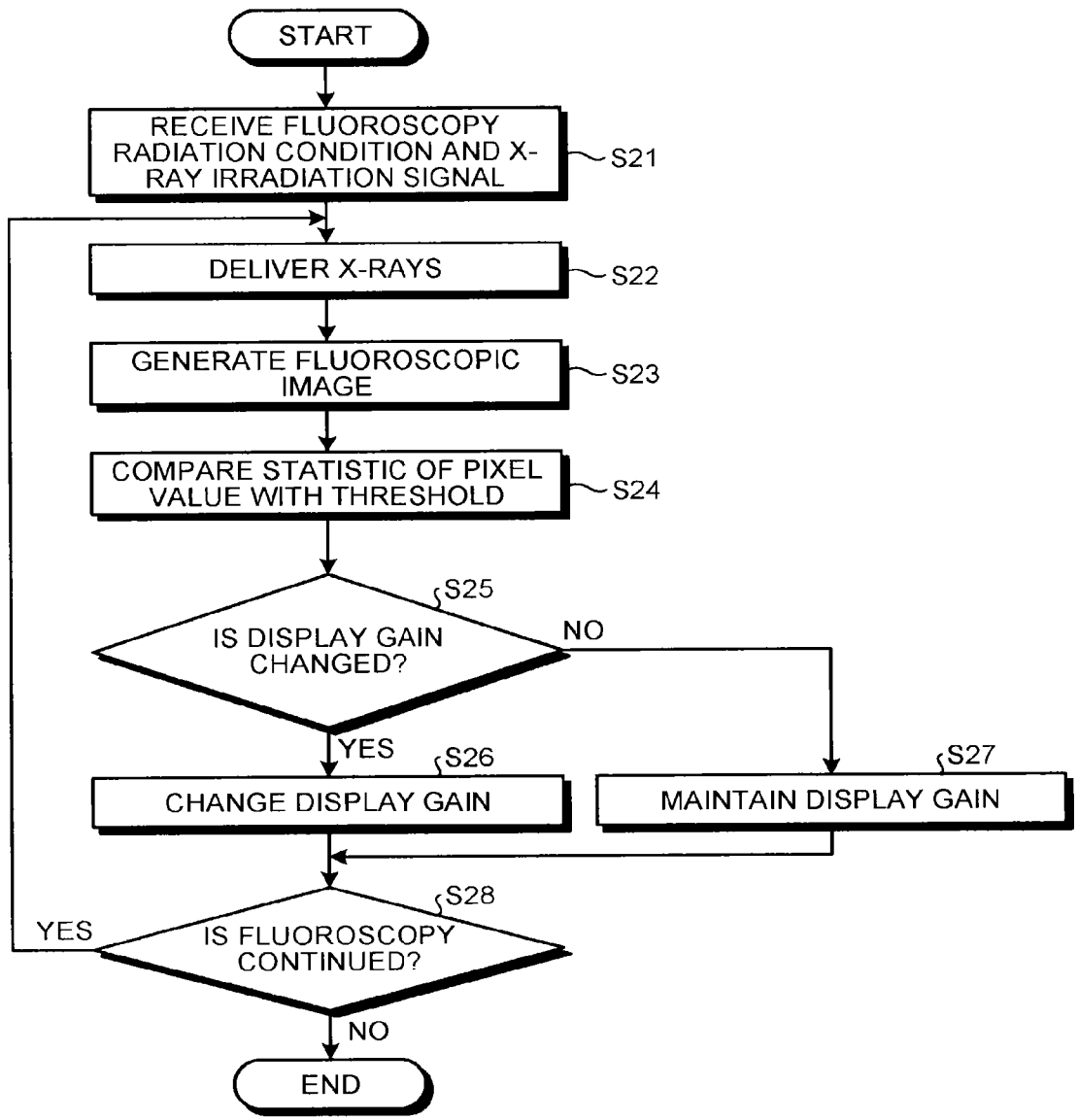
FIG. 13 is a first flow chart for explaining the flow of adjustment of a display gain by an X-ray diagnosis apparatus 1 according to the second embodiment that executes fluoroscopy.
Figure 14:
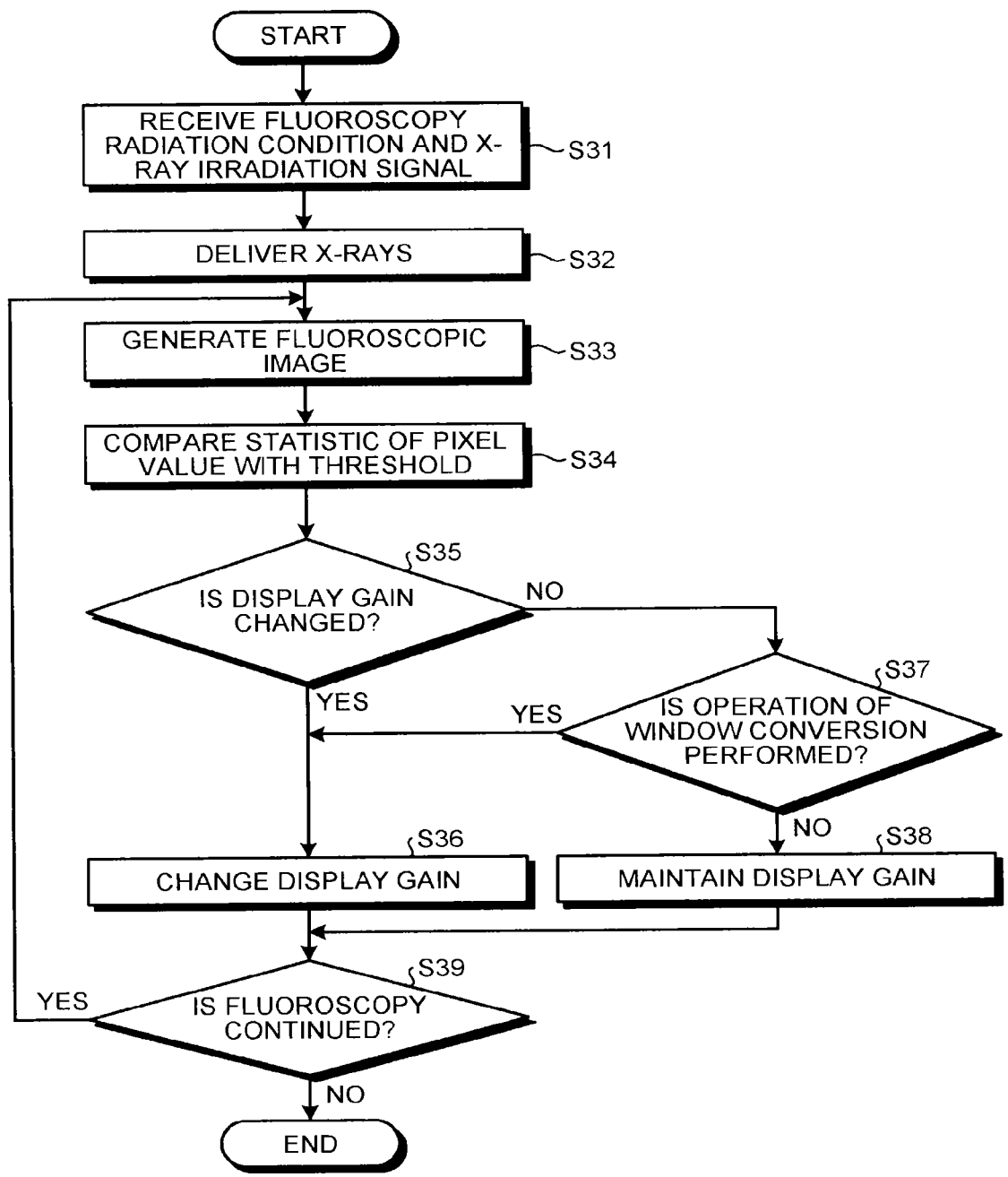
FIG. 14 is a second flow chart for explaining the flow of adjustment of the display gain by the X-ray diagnosis apparatus 1 according to the second embodiment that executes the fluoroscopy.

First, the medical diagnostic imaging apparatus (X-ray diagnosis apparatus 1) according to the second embodiment will be described with reference to FIG. 10 to FIG. 14. FIG. 10 is a schematic block diagram illustrating part of the functional configuration of the display data processing unit 17 according to the second embodiment. FIG. 11 is a diagram for explaining an example of processing in the X-ray diagnosis apparatus 1 according to the second embodiment. FIG. 12 is a diagram illustrating an example of the partial fluoroscopic image generated by the X-ray diagnosis apparatus 1 according to the second embodiment. FIG. 13 is a first flow chart for explaining the flow of adjustment of the display gain by the X-ray diagnosis apparatus 1 according to the second embodiment that executes the fluoroscopy. FIG. 14 is a second flow chart for explaining the flow of adjustment of the display gain by the X-ray diagnosis apparatus 1 according to the second embodiment that executes the fluoroscopy. The content of the display data processing unit 17 in the second embodiment is different from that in the first embodiment. The rest of the configuration is the same as in the X-ray diagnosis apparatus 1 according to the first embodiment. Hereinafter, differences from the first embodiment will be mainly described.

Display Gain Adjusting Unit 174

As illustrated in FIG. 10, the display data processing unit 17 according to the second embodiment includes a display gain adjusting unit 174 in addition to the interface 171, the image adjusting unit 172, and the image synthesizing unit 173. The display gain adjusting unit 174 adjusts the pixel value of the image data, that is, adjusts the display gain. According to the adjustment of the display gain by the display gain adjusting unit 174, the gradation (brightness) of the X-ray image is adjusted. The image data whose display gain is adjusted may be an image data (raw image data) generated by the image generating unit 152 or an image data to which predetermined image processing or image synthesis as described in the first embodiment is applied.

The display gain adjusting unit 174 may have a look-up table for adjusting the display gain by way of example. The look-up table has the format of a comparative table such as to correct (output) the pixel value (input) of the image data to a predetermined pixel value set in advance. In this case, the display gain adjusting unit 174 adjusts the display gain by the look-up table. For example, the display gain adjusting unit 174 corrects the pixel value (gradation) of each pixel in the image data received from the storage unit 156 to an optional pixel value by the look-up table.

Hereinafter, an example of processing in the X-ray diagnosis apparatus 1 according to the second embodiment will be described with reference to FIG. 11. FIG. 11 illustrates a case where the fluoroscopic image (LIH image) is imaged by the general fluoroscopy, the partial fluoroscopic image is imaged thereafter, and a synthetic image is displayed on a monitor (display unit). In such a case, for example, as illustrated in FIG. 11, a preset value (the fluoroscopy radiation condition set in advance in the fluoroscopy radiation condition setting unit 18) is input to the X-ray control unit 12, and then a signal "Xnormal" for causing the X-ray irradiation to be performed in the general fluoroscopy is transmitted to the X-ray tube 3. An image (LIH image) is then generated based on the X-ray detected by the X-ray detecting unit 5, and input to the pixel value arithmetic unit 153.

The pixel value arithmetic unit 153 outputs the statistic $\beta$ of the pixel value in a particular region included in the LIH image to the pixel value comparing unit 154. The pixel value comparing unit 154 compares the input statistic $\beta$ with the threshold $\alpha$ of the pixel value, and transmits an ABC ratio A to the fluoroscopy radiation condition setting unit 18 to perform the ABC. As an example, when a target value level, which is the threshold $\alpha$, is "400" and the statistic $\beta$ is "400", the pixel value comparing unit 154 transmits "ABC ratio A=1" to the fluoroscopy radiation condition setting unit 18.

Here, when the general fluoroscopy is switched to the partial fluoroscopy, the statistic $\beta$ of the pixel value in the particular region of the partial fluoroscopic image calculated by the pixel value arithmetic unit 153 as described above will be decreased. For example, when the statistic $\beta$ of the partial fluoroscopic image becomes "300", an X-ray diagnosis apparatus in the related art transmits the value of a comparison result "400/300" with respect to the target value level "400" that is the threshold $\alpha$, as the ABC ratio A. Accordingly, a signal "Xroi" for causing the X-ray irradiation with a higher dose compared to the preset value to be performed in the partial fluoroscopy is transmitted to the X-ray tube 3. However, when the general fluoroscopy is switched to the partial fluoroscopy, the X-ray diagnosis apparatus 1 according to the second embodiment is controlled to perform the partial fluoroscopy under the fluoroscopy radiation condition of the general fluoroscopy. That is, in the X-ray diagnosis apparatus 1 according to the second embodiment, the signal "Xroi" for causing the X-ray irradiation with the same dose as with the "Xnormal" to be performed is transmitted to the X-ray tube 3 even when the statistic $\beta$ of the partial fluoroscopic image is "300".

As described above, the X-ray diagnosis apparatus 1 according to the second embodiment performs the partial fluoroscopy under the fluoroscopy radiation condition of the general fluoroscopy to prevent an increase in the dose of radiation exposure of the subject at the X-ray imaging. However, the statistic $\beta$ of the pixel value of the partial fluoroscopic image is "300", for example, and is decreased from the statistic "400" of the pixel value of the LIH image in the general fluoroscopy. The display gain adjusting unit 174 according to the second embodiment thus adjusts the display gain of the partial fluoroscopic image based on the statistic of the pixel value of the image input from the pixel value arithmetic unit 153. For example, the display gain adjusting unit 174 adjusts the display gain so that the statistic β of the partial fluoroscopic image is changed from "300" to "400". The display gain may be adjusted by changing the setting of the look-up table. Accordingly, there is almost no difference between the pixel values of the LIH image in the general fluoroscopy and the partial fluoroscopic image. For example, as illustrated in FIG. 12, in the X-ray diagnosis apparatus 1 according to the second embodiment, R1 and R2 can be observed with substantially the same pixel value in the synthetic image of the partial fluoroscopy in which the general region of interest R1 using the LIH image is synthesized with the region of interest for partial fluoroscopy R2 using the partial fluoroscopic image. Because the display gain is always adjusted even when a dynamic image is synthesized with R2, observation can be performed with a stable pixel value.

Operation

Next, the flow of the adjustment of the display gain by the display gain adjusting unit 174 will be described with reference to a flow chart of FIG. 13. In FIG. 13, the flow of the ABC for the adjustment of the fluoroscopy radiation condition is not illustrated.

S21 to S24

In the adjustment of the display gain according to the second embodiment, processing from the start of the fluoroscopy (S21, S22) to the generation of the fluoroscopic image (S23) is the same as in S01 to S03 according to the first embodiment, and the description of this processing is not repeated here. In addition, the calculation of the statistic β and the comparison between the threshold α and the statistic β (S24) are also the same as in S04 according to the first embodiment, so that the description thereof is not repeated here.

S25

The display gain adjusting unit 174 (or the main control unit 121) refers to the comparison result by the pixel value comparing unit 154 and determines whether to change the display gain. When the display gain is adjusted by the look-up table, it is determined whether to change the look-up table.

S26

For example, if the difference (absolute value or the like) or the ratio between the statistic β of the pixel value and the threshold α is larger than a predetermined value (Yes at S25), the display gain adjusting unit 174 (or the main control unit 121) adjusts the display gain of the image data. In a case where the look-up table is used, the display gain adjusting unit 174 adjusts (changes) the set value of the look-up table.

S27

In contrast, if the difference or the ratio between the statistic β of the pixel value and the threshold α is smaller than the predetermined value (No at S25), the display gain adjusting unit 174 (or the main control unit 121) maintains the display gain as it is. Alternatively, the display gain adjusting unit 174 maintains the look-up table as it is.

S28

The determination of whether to continue the fluoroscopy by the pixel value comparing unit 154 (or the main control unit 121) is the same as the processing at S08 according to the first embodiment, so that the description thereof is not repeated here.

As an example, if operation for stopping the X-ray irradiation (stopping the fluoroscopy) is performed, the main control unit 121 stops driving of each component related to the X-ray irradiation (output), such as the high voltage generating unit 122. Accordingly, the X-ray irradiation is stopped. In response to the operation for stopping, the image generating unit 152 causes the storage unit 156 to store therein the LIH image. The main control unit 121 causes a storage unit (not illustrated) to store therein the fluoroscopy radiation condition corresponding to the LIH image.

In the second embodiment, even after the X-ray irradiation control by the X-ray control unit 12 is switched to the partial fluoroscopy, the pixel value arithmetic unit 153 calculates the statistic β of the partial fluoroscopic image generated by the image generating unit 152. Similarly, the pixel value comparing unit 154 compares the statistic β with the threshold α in the partial fluoroscopy. The comparison result by the pixel value comparing unit 154 is used for adjustment of the display gain by the display gain adjusting unit 174 (adjustment of the set value of the look-up table). However, in the second embodiment, the comparison result by the pixel value comparing unit 154 is not used for adjusting a fluoroscopy condition.

The adjustment of the display gain may be performed on raw image data generated by the image generating unit 152, or may be performed on image data to which predetermined image processing or image synthesis is applied (image data to be displayed). For example, the image data to be displayed includes a digital angiographic image, an energy subtraction image, and a 3D road map image.

The image data generated by the collected data processing unit 15 is stored in the storage unit 156 in some cases. When the fluoroscopy is interrupted or completed, the display gain adjusting unit 174 can adjust the display gain of the pixel value in the image data read out from the storage unit 156 by the operator. In this manner, the gradation (brightness) of the X-ray image is adjusted by adjusting the display gain by the display gain adjusting unit 174. Although the display gain adjusting unit 174 adjusts the display gain of the image data as described above, the processing can also be executed through an instruction for window conversion received from the operator.

In such a case, for example, the display gain adjusting unit 174 has a look-up table and adjusts the display gain by the look-up table. That is, the display gain adjusting unit 174 corrects the pixel value (gradation) of each pixel in the X-ray image generated by the image generating unit 152 to a pixel value optionally set by the look-up table. In other words, the display gain adjusting unit 174 adjusts at least either a window level (WL) or a window width (WW) in the generated X-ray image based on the look-up table to perform the window conversion, thereby adjusting the pixel value (brightness value/gray value) of the X-ray image.

Operation

With reference to a flow chart in FIG. 14, the flow of the adjustment of the display gain according to the window conversion will be described. In FIG. 14, the flow of the ABC for the adjustment of the fluoroscopy radiation condition is not illustrated.

S31 to S34

In the adjustment of the display gain described above, processing from the start of the fluoroscopy (S31 and S32) to the generation of the fluoroscopic image (S33) is the same as in S01 to S03 according to the first embodiment, and the description of the processing is not repeated here. The calculation of the statistic β and the comparison between the threshold α and the statistic β (S34) are also the same as in S04 according to the first embodiment, so that the description thereof is not repeated here.

S35

The display gain adjusting unit 174 (or the main control unit 121) refers to the comparison result by the pixel value comparing unit 154 and determines whether to adjust the display gain. When the display gain is adjusted with the look-up table, it is determined whether to change the look-up table.

S36

For example, if the difference (absolute value or the like) or the ratio between the statistic $\beta$ of the pixel value and the threshold $\alpha$ is larger than a predetermined value (Yes at S35), the display gain adjusting unit 174 (or the main control unit 121) adjusts the display gain of the image data. In a case where the look-up table is used, the display gain adjusting unit 174 changes the set value of the look-up table.

S37

In contrast, if the difference or the ratio between the statistic $\beta$ of the pixel value and the threshold $\alpha$ is smaller than the predetermined value (No at S35), the display gain adjusting unit 174 (or the main control unit 121) determines whether there has been an instruction for the operation of the window conversion from the operation unit 162. If there is the instruction for the operation of the window conversion (Yes at S37), the process proceeds to S36, and the display gain adjusting unit 174 (or the main control unit 121) adjusts the display gain of the image data.

S38

In contrast, if there is no instruction for the operation of the window conversion (No at S37), the display gain adjusting unit 174 maintains the display gain as it is. Alternatively, the display gain adjusting unit 174 maintains the look-up table as it is.

S39

The determination of whether to continue the fluoroscopy by the pixel value comparing unit 154 (or the main control unit 121) is the same as the processing at S08 according to the first embodiment, so that the description thereof is not repeated here.

Other Examples

A configuration in which the ratio between the threshold $\alpha$ and the statistic $\beta$ of the pixel value of the partial fluoroscopic image is obtained may be employed. For example, the threshold $\alpha$ is set as an adjustment value of the look-up table for adjusting the display gain in the partial fluoroscopy. In this configuration, the display gain adjusting unit 174 may calculate the ratio between the threshold $\alpha$ and the statistic $\beta$ of the pixel value of the partial fluoroscopic image and change the look-up table based on the calculated ratio.

The set value of the look-up table described above can be adjusted by the operation unit 162 and the like. Because the user can perform an operation to adjust the set value of the look-up table, a gain adjustment of the pixel value (brightness) of the X-ray image by the display gain adjusting unit 174 can be optionally performed. Even the X-ray image once stored may be read out and adjusted to have any brightness.

Action and Effect

The action and effect of the medical diagnostic imaging apparatus according to the second embodiment described above will be described.

The medical diagnostic imaging apparatus according to the embodiment performs the ABC in the general fluoroscopy to adjust the fluoroscopy radiation condition so that an optimal pixel value is obtained, and performs imaging in the partial fluoroscopy with the fluoroscopy radiation condition fixed to the condition at the time of acquiring the LIH image. This prevents an increase in the dose of radiation exposure of the subject in the partial fluoroscopy. The fluoroscopy radiation condition is adjusted by the ABC, so that it is possible to avoid a situation in which a structure in the subject cannot be visually recognized in the partial fluoroscopic image.

In a case where the brightness of each of the images is different because of the difference between the statistic of the pixel value of the LIH image and the statistic of the pixel value of the partial fluoroscopic image, there is a risk that visibility may be hindered. However, in the second embodiment, the display gain of the image data generated by the image generating unit 152 is adjusted according to the brightness of the fluoroscopic image or the partial fluoroscopic image. Accordingly, it is possible to avoid a situation in which the visibility is deteriorated, by causing the brightness of the LIH image to correspond to the brightness of the partial fluoroscopic image.

The collected data processing unit 15 performs the gain adjustment before the image processing by the image adjusting unit 172, so that the image adjusting unit 173 performs the image processing in a state in which the pixel value of the image data has been adjusted. That is, the medical diagnostic imaging apparatus according to the second embodiment can effectively perform the image processing.

In a case where the brightness of each of the images is different because of the difference between the statistic of the pixel value of the LIH image and the statistic of the pixel value of the partial fluoroscopic image, there is a risk that visibility may be hindered. However, in the third embodiment, the window conversion of the partial fluoroscopic image generated by the image generating unit 152 is adjusted according to the brightness of the partial fluoroscopic image. Accordingly, it is possible to avoid a situation in which the visibility is deteriorated, by causing the brightness of the LIH image to correspond to the brightness of the partial fluoroscopic image.

Third Embodiment

The first and the second embodiments above describe the case where the partial fluoroscopy is performed under the fluoroscopy radiation condition of the general fluoroscopy when the general fluoroscopy is switched to the partial fluoroscopy. The third embodiment describes a case where the pixel value is adjusted by causing the ABC to function when the general fluoroscopy is switched to the partial fluoroscopy.

Figure 15:
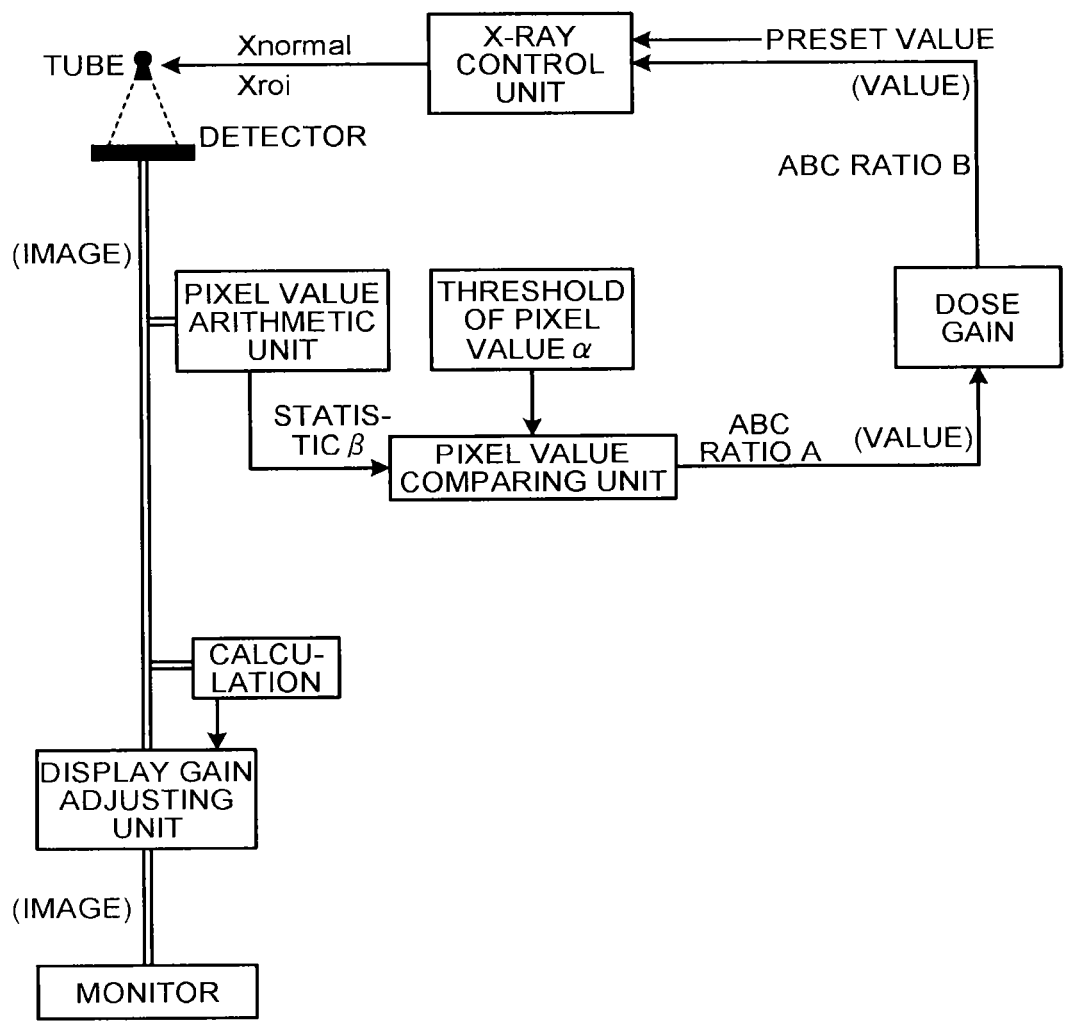
FIG. 15 is a diagram for explaining an example of processing in an X-ray diagnosis apparatus according to a third embodiment.
Figure 16:
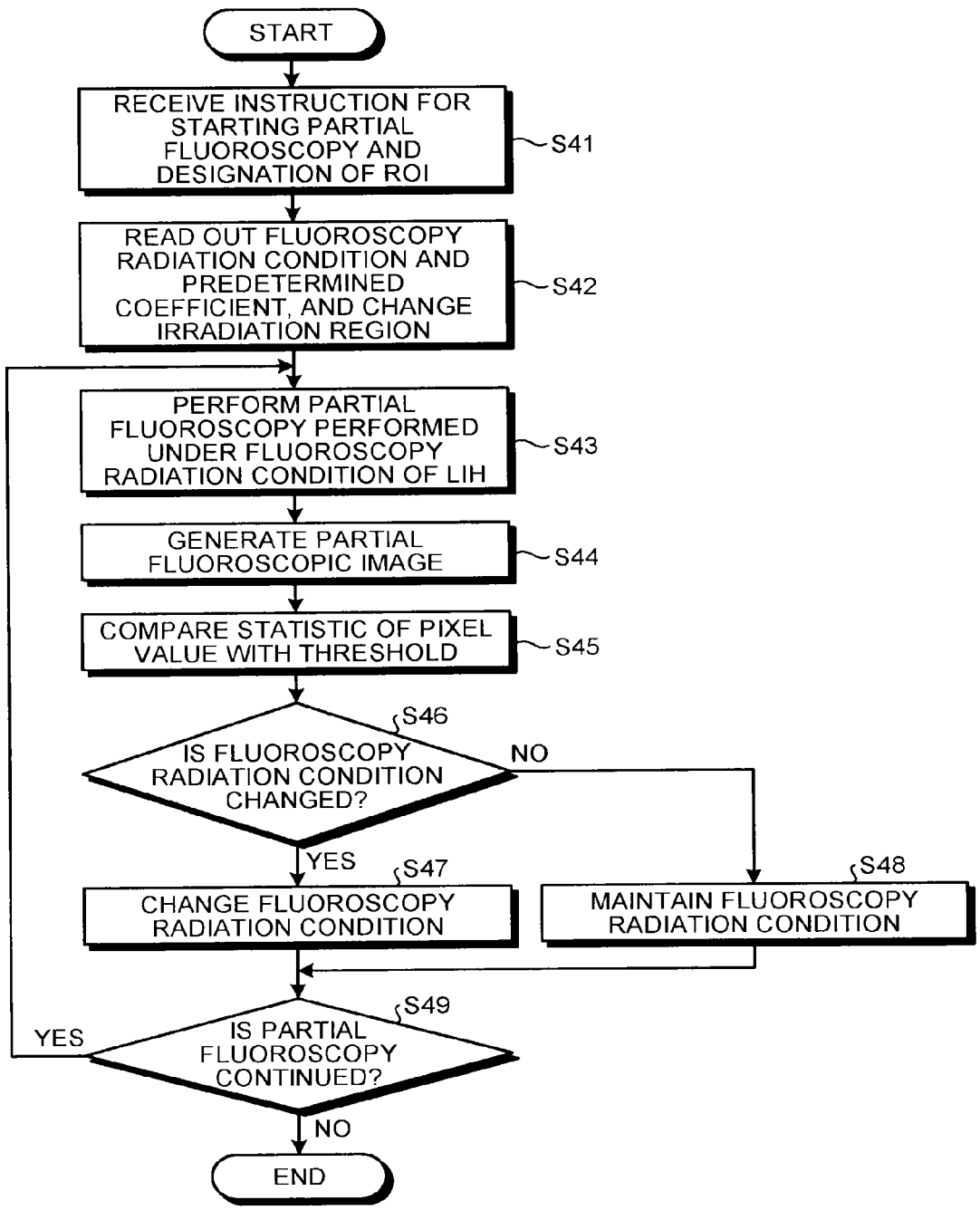
FIG. 16 is a schematic flow chart for explaining the flow of control in the X-ray diagnosis apparatus according to the third embodiment for partial fluoroscopy.

First, a medical diagnostic imaging apparatus (X-ray diagnosis apparatus 1) according to the third embodiment will be described with reference to FIG. 15 and FIG. 16. FIG. 15 is a diagram for explaining an example of processing in the X-ray diagnosis apparatus according to the third embodiment. FIG. 16 is a schematic flow chart for explaining the flow of control in the X-ray diagnosis apparatus 1 according to the third embodiment for the partial fluoroscopy. The third embodiment is different from the first embodiment and the second embodiment in the content of processing and content of control by the collected data processing unit 15 and the X-ray control unit 12 in the partial fluoroscopy. The rest of the configuration is the same as in the X-ray diagnosis apparatus 1 according to the first embodiment and the second embodiment. Hereinafter, differences from the first embodiment and the second embodiment will be mainly described.

In the third embodiment, the ABC is performed in the general fluoroscopy. This is similar to the processing from the start of the fluoroscopy to the adjustment of the fluoroscopy radiation condition based on the statistic β of the image (refer to FIG. 7, S01 to S08) according to the first embodiment. In the first embodiment and the second embodiment, the fluoroscopy radiation condition is not adjusted based on the comparison result between the threshold α and the statistic β when the general fluoroscopy is switched to the partial fluoroscopy. By contrast, in the third embodiment, the comparison result by the pixel value comparing unit 154 is used for adjusting the fluoroscopy radiation condition in some cases. Hereinafter, processing and the configuration of each component according to the third embodiment will be described.

In the medical diagnostic imaging apparatus according to the third embodiment, the control of the general fluoroscopy is switched to the control of the partial fluoroscopy according to a predetermined trigger (operation and the like). In the partial fluoroscopy, the fluoroscopy radiation condition of the stored LIH image is read out, and each control unit such as the X-ray control unit 12 controls each unit such as the high voltage generating unit 122 according to the condition. At this time, the pixel value arithmetic unit 153 calculates the statistic β of the pixel value of the image generated by the image generating unit 152. Correspondingly, the pixel value comparing unit 154 reads out the threshold α from the fluoroscopy radiation condition setting unit 18 and the like and compares it with the statistic β.

In the third embodiment, the comparison result by the pixel value comparing unit 154 or the fluoroscopy radiation condition adjusted based on the comparison result is transmitted to the main control unit 121 in the control of the partial fluoroscopy too. The X-ray control unit 12 according to the third embodiment causes a storage unit (not illustrated) to store therein a predetermined coefficient. In a case where the fluoroscopy radiation condition is adjusted based on the comparison result after the general fluoroscopy is switched to the partial fluoroscopy, the main control unit 121 reads out the predetermined coefficient from the storage unit. The main control unit 121 reflects the read-out predetermined coefficient in the adjusted fluoroscopy radiation condition. The main control unit 121 utilizes the fluoroscopy radiation condition in which the coefficient is reflected, as a control parameter of the high voltage generating unit 122.

For example, a coefficient that reduces irradiation dose of X-rays in the partial fluoroscopy is set as the predetermined coefficient. As an example of the present embodiment, the comparison result received from the pixel value comparing unit 154 is the ratio between the threshold α and the statistic β. For example, the predetermined coefficient may be "0.75". Even when the comparison result obtained by the pixel value comparing unit 154 in the partial fluoroscopy is reflected in the fluoroscopy radiation condition, as illustrated in the above example, control by which the amount of X-ray irradiation is one-fold or less is performed by multiplying the fluoroscopy radiation condition by a coefficient that reduces the dose of X-rays. In contrast, the dose of X-rays delivered in the partial fluoroscopy may be increased by multiplying the predetermined coefficient set in advance by the fluoroscopy radiation condition. In any of these cases, the X-ray control unit 12 controls the fluoroscopy radiation condition by using the ratio between the threshold α and the statistic β to perform control of obtaining a preferred statistic β.

Hereinafter, an example of processing of the X-ray diagnosis apparatus 1 according to the third embodiment will be described with reference to FIG. 15. FIG. 15 illustrates a case where the fluoroscopic image (LIH image) is imaged by the general fluoroscopy, the partial fluoroscopic image is imaged thereafter, and the synthetic image is displayed on the monitor (display unit). In such a case, for example, as illustrated in FIG. 15, a preset value (fluoroscopy radiation condition set in advance in the fluoroscopy radiation condition setting unit 18) is input to the X-ray control unit 12, and a signal "Xnormal" that causes the X-ray irradiation to be executed in the general fluoroscopy is transmitted to the X-ray tube 3. An image (LIH image) is generated based on the X-ray detected by the X-ray detecting unit 5 and input to the pixel value arithmetic unit 153.

The pixel value arithmetic unit 153 calculates the statistic β of the pixel value in a predetermined region included in the LIH image and outputs the calculated statistic β to the pixel value comparing unit 154. The pixel value comparing unit 154 compares the input statistic β with the threshold α of the pixel value, and transmits the ABC ratio A to the fluoroscopy radiation condition setting unit 18 to execute the ABC. When the general fluoroscopy is switched to the partial fluoroscopy, the statistic β of the pixel value in the predetermined region of the partial fluoroscopic image calculated by the pixel value arithmetic unit 153 as described above is reduced. For example, when the statistic β of the LIH image in the general fluoroscopy is "400" while the statistic β of the partial fluoroscopic image is "300", the X-ray diagnosis apparatus 1 transmits a value "400/300" of the comparison result with the threshold α "400" of the pixel value as the ABC ratio A to the fluoroscopy radiation condition setting unit 18 by the ABC.

In the X-ray diagnosis apparatus 1 according to the third embodiment, an increase in the dose of radiation exposure of the subject is prevented by multiplying the predetermined coefficient for adjusting a dose gain by the ABC ratio A. For example, in the X-ray diagnosis apparatus 1 according to the third embodiment, the ABC ratio A "400/300" transmitted to the fluoroscopy radiation condition setting unit 18 is multiplied by a coefficient "0.75". Accordingly, the ABC ratio B illustrated in FIG. 15 is "400/300×0.75"="1". Thus, in the partial fluoroscopy, the signal "Xroi" for causing the X-ray irradiation of the same dose as in the general fluoroscopy to be performed is transmitted to the X-ray tube 3.

As described above, in the X-ray diagnosis apparatus 1 according to the third embodiment, the ratio between the threshold α and the statistic β to be controlled by the ABC is multiplied by the predetermined coefficient to prevent the dose of radiation exposure of the subject from increasing in the X-ray imaging. However, the statistic β of the pixel value of the partial fluoroscopic image is "300", that is, is decreased from the statistic "400" of the pixel value of the LIH image in the general fluoroscopy. Accordingly, also in the X-ray diagnosis apparatus 1 according to the third embodiment, the display gain of the image data is adjusted by the display gain adjusting unit 174. At this time, the display gain adjusting unit 174 adjusts the display gain of the partial fluoroscopic image by multiplying the inverse number of the multiplied predetermined coefficient by the image data of the partial fluoroscopic image. For example, the first gain adjusting unit 155 multiplies "1/0.75" by "300" to adjust the statistic β of the pixel value of the partial fluoroscopic image to "400".

These adjustments may be performed by setting the look-up table (LUT), for example. The predetermined coefficient can be set in advance from the degree of the X-ray aperture when the partial fluoroscopy is performed. The predetermined coefficient described herein is not limited to a fixed value set in advance, and may be automatically changed according to the degree of opening of the X-ray aperture, for example.

As described above, the scattered radiation is decreased due to a narrowed irradiation range in the partial fluoroscopy. Accordingly, the brightness of the image may be decreased. In this case, if the ABC for adjusting the fluoroscopy radiation condition is performed, there is a risk that the dose of radiation exposure of the subject cannot be readily reduced. In this regard, the dose of radiation exposure can be reduced with the configuration and the control as described in the present embodiment.

Partial Fluoroscopy

Next, described will be the control of the X-ray control unit 12 and the process flow of the collected data processing unit 15 according to the third embodiment for the partial fluoroscopy with reference to FIG. 16. FIG. 16 is a schematic flow chart for explaining the flow of control in the medical diagnostic imaging apparatus according to the third embodiment for the partial fluoroscopy. When the operator performs an operation for interrupting the fluoroscopy through the operation unit 162 in a situation in which the X-ray imaging system performs the fluoroscopy in the general region of interest R1, the instruction signal for stopping the X-ray irradiation is transmitted to the X-ray control unit 12. When the operator performs the operation for starting the partial fluoroscopy and designates the region of interest for partial fluoroscopy R2 through the operation unit 162, the X-ray control unit 12 performs the control in the partial fluoroscopy.

S41

Upon receiving the instruction for starting the partial fluoroscopy, the aperture control unit 13 receives the positional information of the region of interest for partial fluoroscopy R2.

S42

Upon receiving the instruction for starting the partial fluoroscopy, the X-ray control unit 12 reads out the fluoroscopy radiation condition corresponding to the LIH image and the information of the predetermined coefficient. The aperture control unit 13 controls the X-ray aperture 4, so that the irradiation field of the X-rays delivered to the subject from the X-ray tube 3 is limited.

S43

The main control unit 121 of the X-ray control unit 12 controls the X-ray irradiation field, the high voltage generating unit 122, and the like and performs the X-ray irradiation (partial fluoroscopy) based on the read-out fluoroscopy radiation condition. At this time, the main control unit 121 receives the information of the predetermined coefficient. The main control unit 121 of the X-ray control unit 12 controls the X-ray irradiation field, the high voltage generating unit 122, and the like and performs the X-ray irradiation (partial fluoroscopy) based on the read-out fluoroscopy radiation condition of the LIH image. At this time, the X-ray irradiation field is a range limited at S42.

S44

When the partial fluoroscopy is started, the image generating unit 152 generates the partial fluoroscopic image.

S45

The pixel value comparing unit 154 (or the main control unit 121) compares the statistic β of the pixel value of the partial fluoroscopic image with the threshold α.

S46

With reference to the comparison result by the pixel value comparing unit 154, it is determined whether to change the fluoroscopy radiation condition such as the X-ray condition.

S47

If the difference between the statistic β of the pixel value and the threshold α is large, the pixel value comparing unit 154 determines to change the fluoroscopy radiation condition such as the X-ray condition (Yes at S46). In this case, the pixel value comparing unit 154 transmits the ratio between the threshold α and the statistic β to the main control unit 121. The main control unit 121 multiplies the read-out predetermined coefficient by the fluoroscopy radiation condition to make an adjustment (change). The main control unit 121 controls the high voltage generating unit 122 according to the adjusted fluoroscopy radiation condition.

S48

If the difference between the statistic of the pixel value and the threshold α is small (No at S46), the pixel value comparing unit 154 (or the main control unit 121) maintains the fluoroscopy radiation condition as it is.

S49

The main control unit 121 determines whether to continue the partial fluoroscopy. This is the same as at S08 of the first embodiment, so that description thereof is not repeated here.

In this embodiment, it is possible to employ the adjustment of the display gain according to the second embodiment. That is, when the fluoroscopy radiation condition is changed at S49, the display gain adjusting unit 174 adjusts the display gain of the image data (partial fluoroscopic image).

Action and Effect

The action and effect of the medical diagnostic imaging apparatus according to the third embodiment described above will be described.

The medical diagnostic imaging apparatus according to the present embodiment performs the preferred ABC in the general fluoroscopy/partial fluoroscopy to adjust the fluoroscopy radiation condition. In the partial fluoroscopy, the fluoroscopy radiation condition is adjusted according to the comparison result by the pixel value comparing unit 154, and is multiplied by the predetermined coefficient, by which the fluoroscopy radiation condition (the dose of X-rays and the like) is reduced for example. For example, when the fluoroscopy radiation condition is adjusted so that the dose of X-rays is reduced, it is possible to reduce the dose of radiation exposure of the subject in the partial fluoroscopy. Because the fluoroscopy radiation condition is adjusted by the ABC, it is possible to avoid a situation in which a structure in the subject cannot be visually recognized in the partial fluoroscopic image.

Fourth Embodiment

Next, the medical diagnostic imaging apparatus (X-ray diagnosis apparatus 1) according to a fourth embodiment will be described. The fourth embodiment is different from the first embodiment to the third embodiment in the control of the X-ray control unit 12. The rest of the configuration is the same as in the X-ray diagnosis apparatus 1 according to the first embodiment to the third embodiment. Hereinafter, differences from the first to the third embodiments will be mainly described.

The adjustment of the fluoroscopy radiation condition in the main control unit 121 may be performed by the pixel value comparing unit 154 instead of the main control unit 121. In such a case, hereinafter, the description of the main control unit 121 about the adjustment of the fluoroscopy radiation condition may be read as the processing by the image generating unit 152.

In the fourth embodiment, when the brightness of the fluoroscopic image is changed as an adjustment of the fluoroscopy radiation condition in the ABC, especially the X-ray condition (tube voltage (kV), tube current (A), irradiation time (s)), the main control unit 121 adjusts the tube voltage (kV) in preference to the tube current (A) and the irradiation time (s).

However, when the statistic $\beta$ of the brightness of the fluoroscopic image is higher than the threshold $\alpha$ (for example, "$\alpha-\beta \leq 0$"), the tube current (A) and the irradiation time (s) are preferentially adjusted. This is because the X-ray dose is decreased if the parameters of the tube current (A) and the irradiation time (s) are lowered, so that the dose of radiation exposure of the subject can be reduced.

In the ABC in the X-ray control unit 12 according to the fourth embodiment, for example, when the pixel value (brightness) of the fluoroscopic image is smaller than a predetermined value in comparison to the threshold, the X-ray condition is adjusted. At this time, if the tube current (A) and the irradiation time (s) are adjusted as an adjustment of the pixel value of the fluoroscopic image, the X-ray dose is increased. Accordingly, the dose of radiation exposure of the subject may be increased. Insufficiency of the brightness of the fluoroscopic image may be addressed by increasing the brightness of the fluoroscopic image by increasing the tube voltage (kV).

If the tube voltage (kV) is raised, the X-ray energy is increased and the X-rays can easily pass through a structure in the subject. This may affect the contrast of the X-ray image and thus is effective in the ABC according to the fourth embodiment for observation of a structure in which the pixel value tends to be increased when imaged, such as a catheter. However, in terms of reduction of the dose of radiation exposure, the medical diagnostic imaging apparatus according to the fourth embodiment is effective in any X-ray imaging regardless of whether to observe a structure of which pixel value is high.

In the ABC according to the fourth embodiment, although the main control unit 121 preferentially adjusts the tube voltage (kV), the main control unit 121 may be able to adjust the tube current (A) and the irradiation time (s). In such a configuration, for example, the main control unit 121 determines whether to adjust the tube current (A) and the irradiation time (s) depending on the degree of difference between the brightness of the fluoroscopic image and the threshold. That is, if the difference between the statistic $\beta$ of the pixel value of the fluoroscopic image and the threshold $\alpha$ is large as a comparison result by the pixel value comparing unit 154, the main control unit 121 adjusts the tube current (A), the irradiation time (s), and the tube voltage (kV) as the X-ray condition. If the difference is not large, the main control unit 121 does not adjust the tube current (A) or the irradiation time (s) but adjusts only the tube voltage (kV).

The determination of the degree of the comparison result by the pixel value comparing unit 154, that is, the determination of whether the difference between the statistic $\beta$ and the threshold $\alpha$ is large can be performed by setting a range of difference (threshold) in advance. Specifically, the pixel value comparing unit 154 is caused to store therein the range of difference between the statistic $\beta$ of the pixel value of the fluoroscopic image and the threshold $\alpha$ in advance. The pixel value comparing unit 154 determines whether the difference is within the range. If the statistic $\beta$ of the pixel value of the fluoroscopic image is out of the predetermined range (for example, "$\alpha-(\beta>100$"), the main control unit 121 determines that the difference between the statistic $\beta$ and the threshold $\alpha$ is large. In such a case, the main control unit 121 adjusts both the tube current (A) and irradiation time (s), and the tube voltage (kV), as the ABC. If the statistic $\beta$ of the fluoroscopic image is out of the predetermined range (for example, "$\alpha-(\beta \leq 100$"), the main control unit 121 determines that the difference between the statistic $\beta$ and the threshold $\alpha$ is small. In such a case, the main control unit 121 does not adjust the tube current (A) and the irradiation time (s), but adjusts only the tube voltage (kV) as the ABC.

As another example, the main control unit 121 may be set so as not to adjust the tube current (A) and the irradiation time (s) in any case.

Action and Effect

The action and effect of the medical diagnostic imaging apparatus according to the fourth embodiment described above will be described.

The medical diagnostic imaging apparatus according to the present embodiment performs the ABC in the general fluoroscopy to adjust the fluoroscopy radiation condition so that an optimal pixel value is obtained, and performs imaging with the fluoroscopy radiation condition fixed to the condition at the time of acquiring the LIH in the partial fluoroscopy. This prevents an increase in the dose of radiation exposure of the subject in the partial fluoroscopy. The fluoroscopy radiation condition is adjusted by the ABC, so that it is possible to avoid a situation in which a structure in the subject cannot be visually recognized in the partial fluoroscopic image.

In the general fluoroscopy, the main control unit 121 is configured to adjust the tube voltage (kV) in preference to the tube current (A) and the irradiation time (s), or adjust only the tube voltage (kV). This reduces the dose of radiation exposure of the subject by preventing an increase in the X-ray dose delivered to the subject by the ABC.

Modification/Combination with Second Embodiment

The medical diagnostic imaging apparatus according to the fourth embodiment is configured to adjust the tube voltage (kV) in preference to the tube current (A) and the irradiation time (s) in the ABC as described above. However, the fourth embodiment is not limited thereto. For example, in addressing the insufficiency of the brightness of the fluoroscopic image, the apparatus may be configured to adjust the brightness (gradation) based on the pixel value of the image generated by the image generating unit 152 as in the second embodiment, instead of adjusting the tube current (A) and the irradiation time (s).

That is, the pixel value comparing unit 154 transmits the comparison result between the statistic $\beta$ and the threshold $\alpha$ to the display gain adjusting unit 174. The display gain adjusting unit 174 receives the comparison result from the pixel value comparing unit 154 and changes the look-up table according to the comparison result. If the window conversion is performed on the partial fluoroscopic image by the changed look-up table, for example, the pixel value (brightness) of the partial fluoroscopic image is increased, and the visibility of the partial fluoroscopic image can be enhanced.

According to the configuration of the modification, the adjustment of the display gain by the display gain adjusting unit 174 is performed in preference to the X-ray condition as the ABC. That is, the ABC is configured so as not to increase the tube current (A), the irradiation time (s), or the tube voltage (kV). An increase in the dose of radiation exposure of the subject due to the increase in the X-ray irradiation dose can be thus avoided, and an influence on the contrast of the X-ray image due to the increase in the X-ray energy can also be avoided.

In the ABC according to the fourth embodiment, the change of the look-up table and the adjustment of the X-ray condition can be used at the same time. However, in this configuration, processing for changing the look-up table by the display gain adjusting unit 174 is performed in preference to the adjustment of the X-ray condition. In this case, as described above, the main control unit 121 determines whether to adjust the X-ray condition depending on the degree of difference between the brightness of the fluoroscopic image and the threshold.

In such ABC, as described above, the main control unit 121 may be caused to determine whether to adjust the tube current (A) and the irradiation time (s). This determination and the subsequent processing have been described hereinabove, so that the description thereof is not repeated.

Fifth Embodiment

Next, the medical diagnostic imaging apparatus (X-ray diagnosis apparatus 1) according to a fifth embodiment will be described. The fifth embodiment is different from the first embodiment to the fourth embodiment in the processing of the image adjusting unit 173. The rest of the configuration is the same as in the X-ray diagnosis apparatus 1 according to the first embodiment to the fourth embodiment. Hereinafter, differences from the first to the fourth embodiments will be mainly described.

Similarly to the first embodiment to the fourth embodiment, the image adjusting unit 173 receives the detection data or the image data from the image generating unit 152 and performs image processing. The image adjusting unit 173 performs image processing such as sharpening of the image, noise reduction, improvement in S/N ratio, edge enhancement. When the general fluoroscopy is switched to the partial fluoroscopy, the image adjusting unit 173 according to the fifth embodiment performs image processing that is different from general image processing.

In the partial fluoroscopy, the region of interest is switched to the region of interest for partial fluoroscopy R2, so that the region of interest is limited and the scattered radiation is reduced. Sharpness of the partial fluoroscopic image may be enhanced because of the reduction in the scattered radiation. The image adjusting unit 173 according to the fifth embodiment performs image processing for further enhancing the sharpness. For example, the image adjusting unit 173 performs processing such as noise suppression, edge detection, and enhancement of the predetermined pixel value, on the partial fluoroscopic image. The above image processing is performed by a spatial filter or a time filter.

The image adjusting unit 173 according to the fifth embodiment may perform the processing for suppressing noise without relying on image processing by the spatial filter or the time filter. For example, the image adjusting unit 173 may calculate a necessary signal and unnecessary noise in real time for each pixel of the partial fluoroscopic image to extract the signal. This reduces the noise without increasing the X-ray dose. By using such a method for reducing the noise, the sharpness can be maintained because a noise removal scheme by the time filter or frequency conversion is not used.

Combination with the Fourth Embodiment

The fourth embodiment is configured so as not to adjust the tube current (A) or the irradiation time (s) in the ABC. Therefore, depending on an X-ray irradiation dose, noise has to be suppressed or the image has to be sharpened in the fluoroscopic image or the partial fluoroscopic image in some cases. The above problem is addressed by the image processing by the image adjusting unit 173. For example, when the ABC is performed, the image adjusting unit 173 further enhances image processing related to noise suppression, sharpening of the image, or edge detection/enhancement in comparison to the image processing in the case of the X-ray imaging without the ABC. In fluoroscopy and partial fluoroscopy, the image adjusting unit 173 enhances the pixel value indicating an ablation catheter and performs the edge detection of the ablation catheter. Accordingly, the ablation catheter in the subject is enhanced and displayed in the partial fluoroscopic image and the like. In addition, the image adjusting unit 173 enhances a recursive filter to suppress noise in the fluoroscopic image or the partial fluoroscopic image.

Action and Effect

The action and effect of the medical diagnostic imaging apparatus according to the fifth embodiment described above will be described.

The medical diagnostic imaging apparatus according to the present embodiment performs the ABC in the general fluoroscopy to adjust the fluoroscopy radiation condition so that an optimal pixel value is obtained, and performs imaging in the partial fluoroscopy with the fluoroscopy radiation condition fixed to the condition at the time of acquiring the LIH image. This prevents an increase in the dose of radiation exposure of the subject in the partial fluoroscopy. The fluoroscopy radiation condition is adjusted by the ABC, so that it is possible to avoid a situation in which a structure in the subject cannot be visually recognized in the partial fluoroscopic image.

The image adjusting unit 173 according to the fifth embodiment performs processing such as noise suppression, edge detection, and enhancement of the predetermined pixel value to further enhance the sharpness of the partial fluoroscopic image. As another example, the image adjusting unit 173 calculates a necessary signal and unnecessary noise in real time for each pixel of the X-ray image to extract the signal. This enables sharpening of the image and noise suppression without increasing the X-ray irradiation dose.

Sixth Embodiment

Next, the medical diagnostic imaging apparatus (X-ray diagnosis apparatus 1) according to a sixth embodiment will be described. The sixth embodiment is different from the first and the second embodiments in the processing of the X-ray control unit 12 and the collected data processing unit 15. The rest of the configuration is the same as in the X-ray diagnosis apparatus 1 according to the first and the second embodiments. Hereinafter, differences from the sixth embodiment will be mainly described.

As described above, the medical diagnostic imaging apparatus performs the partial fluoroscopy by fixing the X-ray condition to the X-ray condition of the LIH image. The region of interest for general fluoroscopy R1 and the region of interest for partial fluoroscopy R2 have different ranges, so that the X-ray condition of the LIE image does not always correspond to the region of interest for partial fluoroscopy R2. Consequently, the brightness of the LIH image is different from the brightness of the partial fluoroscopic image, so that the visibility of the synthetic image of the partial fluoroscopic image and the LIH image may be affected in some cases. Hereinafter, described will be the processing with respect to the influence on the visibility as described above by the medical diagnostic imaging apparatus according to the sixth embodiment.

Enhancement of Partial Fluoroscopic Image

The pixel value arithmetic unit 153 calculates the statistic β1 of the pixel value of the LIH image in advance, and causes a storage unit (not illustrated) to store therein the statistic β1. The pixel value arithmetic unit 153 sequentially calculates the statistic β2 of the pixel value of the partial fluoroscopic image generated by the image generating unit 152. The pixel value comparing unit 154 sequentially compares the statistic β1 of the pixel value of the LIH image with the statistic β2 of the pixel value of the partial fluoroscopic image. The pixel value comparing unit 154 transmits the comparison result to the display gain adjusting unit 174. On the basis of the comparison result, the display gain adjusting unit 174 adjusts the brightness of the partial fluoroscopic image by the look-up table so that the partial fluoroscopic image looks brighter than the LIH image.

For example, the storage unit 156 stores therein in advance a threshold δ by which the statistic β2 of the pixel value of the partial fluoroscopic image is higher than the statistic β1 of the pixel value of the LIH image by a predetermined amount. To cause the partial fluoroscopic image to be brighter than the LIH image, the statistic β2 is set to be higher than the statistic β1 by the predetermined amount. The threshold δ is set such that β2 is higher than β1 by the "predetermined amount".

When the partial fluoroscopy is started, the display gain adjusting unit 174 reads out the threshold δ from the storage unit 156. The display gain adjusting unit 174 receives the comparison result from the pixel value comparing unit 154. If the comparison result (β1−β2) is equal to or less than the threshold δ, the display gain adjusting unit 174 changes the look-up table so as to increase the brightness value of the partial fluoroscopic image. The display gain adjusting unit 174 adjusts the pixel value of the partial fluoroscopic image by the changed look-up table. The display gain adjusting unit 174 may be configured to change the look-up table when the statistic β2 is determined to be lower than the statistic β1. Accordingly, the partial fluoroscopic image looks brighter than the LIH image, so that it is possible to cause the operator to pay attention to the region of interest for partial fluoroscopy R2.

Enhancement of LIH Image

In contrast to the case where the partial fluoroscopic image looks brighter as described above, the partial fluoroscopic image can be configured to look darker than the LIH image. For example, the storage unit 156 stores therein in advance a threshold δ by which the statistic 132 of the pixel value of the partial fluoroscopic image is lower than the statistic β1 of the pixel value of the LIH image by a predetermined amount.

When the partial fluoroscopy is started, the display gain adjusting unit 174 reads out the threshold δ from the storage unit 156. The display gain adjusting unit 174 receives the comparison result from the pixel value comparing unit 154. If the comparison result (β2−β1) is higher than the threshold δ, the display gain adjusting unit 174 changes the look-up table so as to decrease the brightness value of the partial fluoroscopic image. The display gain adjusting unit 174 adjusts the pixel value of the partial fluoroscopic image by the changed look-up table. The display gain adjusting unit 174 may be configured to change the look-up table when the statistic β2 is determined to be higher than the statistic β1. Accordingly, the partial fluoroscopic image looks darker than the LIH image.

Adjustment of Pixel Value of LIH Image

The collected data processing unit 15 described above adjusts the brightness value of the partial fluoroscopic image. However, the configuration is not limited thereto, and the brightness value of the LIH image may be adjusted. That is, as described above, the pixel value arithmetic unit 153 and the pixel value comparing unit 154 transmit the comparison result between the statistic β1 and the statistic β2 to the display gain adjusting unit 174. The storage unit 156 stores therein the threshold δ as described above. If the comparison result (β2−β1) by the pixel value comparing unit 154 is equal to or less than the threshold δ, the look-up table is changed so that the brightness value of the LIH image is lower. The display gain adjusting unit 174 adjusts the pixel value of the LIH image by the changed look-up table. Accordingly, the partial fluoroscopic image looks brighter than the LIH image, so that it is possible to cause the operator to pay attention to the region of interest for partial fluoroscopy R2.

It is also possible to increase the brightness value of the LIH image to cause the partial fluoroscopic image to look relatively dark. This processing is substantially the same as the "Enhancement of LIH Image" described above, so that the description thereof is not repeated here.

Other Examples

The pixel value comparing unit 154 is not necessarily configured to obtain the difference between the statistic β1 and the statistic β2 as described above. Alternatively, the pixel value comparing unit 154 may be configured to obtain the ratio between the threshold α2 and the statistic β2 of the pixel value of the partial fluoroscopic image. For example, when the threshold of the ABC in the general fluoroscopy is assumed to be α1, the threshold α2 is set to be higher than the threshold al as the adjustment value of the look-up table of the gain adjustment in the partial fluoroscopy. In this configuration, the display gain adjusting unit 174 may obtain the ratio between the threshold α2 and the statistic β2 of the pixel value of the partial fluoroscopic image, and change the look-up table based on the obtained ratio.

The threshold α2 may be set to be lower than the threshold al. The display gain adjusting unit 174 may obtain the ratio between the threshold α2 and the statistic β2 of the pixel value of the partial fluoroscopic image, and change the look-up table based on the obtained ratio.

User Interface 16

The adjustment of the brightness value of the partial fluoroscopic image or the adjustment of the brightness value of the LIH image described above is set by the operator via the user interface 16. For example, the operator can set the partial fluoroscopic image to be relatively brighter via the user interface 16. The operator may set the brightness value of the LIH image to be lower via the user interface 16.

Action and Effect

The action and effect of the medical diagnostic imaging apparatus according to the sixth embodiment described above will be described.

The medical diagnostic imaging apparatus according to the present embodiment performs the ABC in the general fluoroscopy to adjust the fluoroscopy radiation condition so that an optimal pixel value is obtained, and performs imaging in the partial fluoroscopy with the fluoroscopy radiation condition fixed to the condition at the time of acquiring the LIH image. This prevents an increase in the dose of radiation exposure of the subject in the partial fluoroscopy. The fluoroscopy radiation condition is adjusted by the ABC, so that it is possible to avoid a situation in which a structure in the subject cannot be visually recognized in the partial fluoroscopic image.

The medical diagnostic imaging apparatus according to the present embodiment can adjust the brightness value of the partial fluoroscopic image or the LIH image to cause the partial fluoroscopic image or the LIH image to be relatively brighter or darker via the user interface 16. Thus, a situation in which the visibility of the synthetic image is affected by the difference between the brightness of the LIH image and the brightness of the partial fluoroscopic image can be avoided.

The above-described medical diagnostic imaging apparatuses according to the first embodiment to the sixth embodiment may be appropriately combined. By combining the embodiments in an appropriate manner, the dose of radiation exposure of the subject can be securely reduced, and deterioration in the visibility of the fluoroscopic image and the partial fluoroscopic image can also be securely prevented.

The above-described first embodiment to the sixth embodiment and the combinations thereof may be applied not only to the X-ray diagnosis apparatus but also to the X-ray CT apparatus.

The medical diagnostic imaging apparatus according to at least one of the above-described embodiments reduces the dose of X-rays in the partial fluoroscopy in comparison to that in the fluoroscopy on a general imaging area. This reduces the dose of radiation exposure of the subject.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical diagnostic imaging apparatus, comprising: processing circuitry configured to
    acquire a plurality of first X-ray images chronologically in a first X-ray irradiation area while adjusting an operating condition by feedback control using a statistic of a pixel value of each first X-ray image and a threshold set in advance; and
    acquire, after acquiring the plurality of first X-ray images, a plurality of second X-ray images chronologically in a second X-ray irradiation area that is narrower than the first X-ray irradiation area while maintaining the adjusted operating condition adjusted at the time of acquiring an acquired first X-ray image of the plurality of first X-ray images.

2. The medical diagnostic imaging apparatus according to claim 1, wherein the processing circuitry is further configured to adjust a display gain of an acquired second X-ray image of the plurality of second X-ray images so that a statistic of a pixel value of the acquired second X-ray image approaches the threshold set in advance.

3. The medical diagnostic imaging apparatus according to claim 2, wherein the processing circuitry is further configured to
    calculate the statistic of the pixel value of the acquired second X-ray image based on the adjusted operating condition and compare the statistic with the threshold, and
    reflect a coefficient set in advance in a result of the comparison and adjust a new operating condition to cause the new operation condition to approach the adjusted operating condition, and
    adjust the display gain of the acquired second X-ray image based on the result of the comparison.

4. The medical diagnostic imaging apparatus according to claim 2, wherein the processing circuitry is further configured to compare the pixel value of the acquired first X-ray image with the pixel value of the acquired second X-ray image, and adjust the display gain of the acquired second X-ray image so that the pixel value of the acquired second X-ray image is higher than the pixel value of the acquired first X-ray image by a predetermined value.

5. The medical diagnostic imaging apparatus according to claim 2, wherein the processing circuitry is further configured to compare the pixel value of the acquired first X-ray image with the pixel value of the acquired second X-ray image, and adjust the display gain of the acquired second X-ray image so that the pixel value of the acquired second X-ray image is lower than the pixel value of the acquired first X-ray image by a predetermined value.

6. The medical diagnostic imaging apparatus according to claim 2, wherein the processing circuitry is further configured to perform both an adjustment of the display gain of the acquired first X-ray image and an adjustment of the display gain of the acquired second X-ray image, and the threshold in the adjustment of the display gain of the acquired second X-ray image is set to be lower than the threshold in the adjustment of the display gain of the acquired first X-ray image.

7. The medical diagnostic imaging apparatus according to claim 2, wherein the processing circuitry is further configured to perform both an adjustment of the display gain of the acquired first X-ray image and an adjustment of the display gain of the acquired second X-ray image, and the threshold in the adjustment of the display gain of the acquired second X-ray image is set to be higher than the threshold in the adjustment of the display gain of the acquired first X-ray image.

8. The medical diagnostic imaging apparatus according to claim 2, wherein the processing circuitry is further configured to
    adjust the display gain based on a correlation between the pixel value of the acquired second X-ray image and a gradation,
    set the threshold of the pixel value of the second X-ray image to be higher than the threshold of the pixel value of the acquired first X-ray image, and
    obtain a ratio between the statistic of the pixel value of the acquired second X-ray image and the threshold to reflect the ratio in the correlation.

9. The medical diagnostic imaging apparatus according to claim 2, wherein the processing circuitry is further configured to
    adjust the display gain based on a correlation between the pixel value of the acquired second X-ray image and a gradation,
    set the threshold of the pixel value of the acquired second X-ray image to be lower than the threshold of the pixel value of the acquired first X-ray image, and
    obtain a ratio between the statistic of the pixel value of the acquired second X-ray image and the threshold to reflect the ratio in the correlation.

10. The medical diagnostic imaging apparatus according to claim 1, wherein the processing circuitry is further configured to receive an operation for adjusting a display gain of an acquired second X-ray image, adjust the display gain of the acquired second X-ray image according to the operation received, and perform control for causing a display to display the acquired second X-ray image whose display gain is adjusted.

11. The medical diagnostic imaging apparatus according to claim 10, wherein the processing circuitry is further configured to adjust the display gain of the acquired second X-ray image based on a correlation between a pixel value of the acquired second X-ray image and a gradation, set the threshold of the pixel value of the acquired second X-ray image to be higher than the threshold of the pixel value of the acquired first X-ray image, and obtain a ratio between the statistic of the pixel value of the acquired second X-ray image and the threshold to reflect the ratio in the correlation.

12. The medical diagnostic imaging apparatus according to claim 10, wherein the processing circuitry is further configured to adjust the display gain of the acquired second X-ray image based on a correlation between a pixel value of the acquired second X-ray image and a gradation, set the threshold of the pixel value of the acquired second X-ray image to be lower than the threshold of the pixel value of the acquired first X-ray image, and obtain a ratio between the statistic of the pixel value of the acquired second X-ray image and the threshold to reflect the ratio in the correlation.

13. The medical diagnostic imaging apparatus according to claim 1, further comprising an X-ray source configured to output X-rays, and wherein the operating condition includes at least one of a tube voltage, a tube current, and a pulse width in X-ray output by the X-ray source.

14. The medical diagnostic imaging apparatus according to claim 13, wherein the processing circuitry is further configured to adjust the tube voltage in preference to the tube current and the pulse width in adjusting the operating condition.

15. The medical diagnostic imaging apparatus according to claim 1, wherein the processing circuitry is further configured to generate a synthetic image of the acquired first X-ray image and the acquired second X-ray image based on a positional relation between the first X-ray irradiation area and the second X-ray irradiation area, and perform control for causing a display to display the synthetic image each time the synthetic image is generated.

16. The medical diagnostic imaging apparatus according to claim 1, wherein the processing circuitry is further configured to execute a filtering process for improving image quality of the plurality second X-ray images.

17. A medical diagnostic imaging apparatus, comprising: processing circuitry configured to capture a subject in a second X-ray irradiation area that is narrower than a first X-ray irradiation area after imaging the subject in the first X-ray irradiation area;

generate a first X-ray image in the first X-ray irradiation area and a second X-ray image in the second X-ray irradiation area based on an imaging result;

calculate a statistic of a pixel value of the first X-ray image and adjust an operating condition of the imaging the subject in the first X-ray irradiation area so that the statistic approaches a threshold set in advance;

control, after generating the first X-ray image, generating of the second X-ray image so as to generate the second X-ray image based on the adjusted operating condition; and adjust a display gain of the second X-ray image so that the statistic of the pixel value of the second X-ray image generated approaches the threshold set in advance.

18. The medical diagnostic imaging apparatus according to claim 17, wherein the processing circuitry is further configured to calculate the statistic of the pixel value of the second X-ray image generated based on the operating condition and compare the statistic with the threshold, reflect a coefficient set in advance in a result of the comparison and adjust a new operating condition to cause the new operation condition to approach the operating condition, and adjust the display gain of the second X-ray image based on the result of the comparison.

19. The medical diagnostic imaging apparatus according to claim 17, wherein the processing circuitry is further configured to compare the pixel value of the first X-ray image with the pixel value of the second X-ray image, and adjust the display gain of the second X-ray image so that the pixel value of the second X-ray image is higher than the pixel value of the first X-ray image by a predetermined value.

20. The medical diagnostic imaging apparatus according to claim 17, wherein the processing circuitry is further configured to compare the pixel value of the first X-ray image with the pixel value of the second X-ray image, and adjust the display gain of the second X-ray image so that the pixel value of the second X-ray image is lower than the pixel value of the first X-ray image by a predetermined value.

* * * * *